US010745355B2

(12) United States Patent
Munoz et al.

(10) Patent No.: US 10,745,355 B2
(45) Date of Patent: Aug. 18, 2020

(54) ANTI-CANCER COMPOUNDS

(71) Applicant: THE UNIVERSITY OF SYDNEY, New South Wales (AU)

(72) Inventors: Lenka Munoz, New South Wales (AU); Fadi Maged Shokry Gurgis, New South Wales (AU); Mia Akerfeldt, New South Wales (AU); Michael Kassiou, New South Wales (AU)

(73) Assignee: THE UNIVERSITY OF SYDNEY, New South Wales (AU)

( * ) Notice: Subject to any disclaimer, the term of this patent is extended or adjusted under 35 U.S.C. 154(b) by 0 days.

(21) Appl. No.: 15/547,227

(22) PCT Filed: Jan. 29, 2016

(86) PCT No.: PCT/AU2016/050044
§ 371 (c)(1),
(2) Date: Jul. 28, 2017

(87) PCT Pub. No.: WO2016/119017
PCT Pub. Date: Aug. 4, 2016

(65) Prior Publication Data
US 2018/0273478 A1 Sep. 27, 2018

(30) Foreign Application Priority Data

Jan. 30, 2015 (AU) ................................ 2015900287
Aug. 20, 2015 (AU) ................................ 2015903380

(51) Int. Cl.
| | |
|---|---|
| *A61K 31/505* | (2006.01) |
| *A61K 31/47* | (2006.01) |
| *A61K 31/44* | (2006.01) |
| *A61K 31/195* | (2006.01) |
| *A61K 31/192* | (2006.01) |
| *C07D 213/61* | (2006.01) |
| *C07D 215/14* | (2006.01) |
| *C07D 239/26* | (2006.01) |
| *C07D 239/34* | (2006.01) |
| *C07C 233/11* | (2006.01) |
| *C07C 233/29* | (2006.01) |
| *C07D 213/56* | (2006.01) |
| *C07C 237/20* | (2006.01) |
| *A61P 35/00* | (2006.01) |

(52) U.S. Cl.
CPC ............ *C07D 213/61* (2013.01); *A61P 35/00* (2018.01); *C07C 233/11* (2013.01); *C07C 233/29* (2013.01); *C07C 237/20* (2013.01); *C07D 213/56* (2013.01); *C07D 215/14* (2013.01); *C07D 239/26* (2013.01); *C07D 239/34* (2013.01)

(58) Field of Classification Search
None
See application file for complete search history.

(56) References Cited

U.S. PATENT DOCUMENTS

| | | | |
|---|---|---|---|
| 3,859,338 A | 1/1975 | Engel et al. | |
| 5,196,543 A | 3/1993 | Jarreau et al. | |
| 5,756,507 A | 5/1998 | Goulet et al. | |
| 2007/0254913 A1 | 11/2007 | Dunn et al. | |
| 2013/0267712 A1 | 10/2013 | Klumpp et al. | |
| 2015/0079154 A1 | 3/2015 | Zender et al. | |

FOREIGN PATENT DOCUMENTS

| | | |
|---|---|---|
| AT | 336594 B | 5/1977 |
| WO | 1991/019730 A1 | 12/1991 |
| WO | 03000694 A1 | 1/2003 |
| WO | 2013/007708 A1 | 1/2013 |
| WO | 2014142755 A1 | 9/2014 |

OTHER PUBLICATIONS

CAS RN: 1579392-33-8, STN entry date Apr. 4, 2014, Chemical name: Benzeneacetamide, 4-amino-N-[2-[4-(1H-pyrazol-1-yl)phenyl]ethyl].
CAS RN: 1458569-90-8, STN entry date Oct. 16, 2013, Chemical name: Guanidine, N-[2-(3-fluorophenyl)ethyl]-N'-phenyl.
CAS RN: 1444316-73-7, STN entry date Jul. 16, 2013, Chemical name: Benzeneacetamide, N-[2-(2-bromophenyl)ethyl]-4-hydroxy.
CAS RN: 1457495-24-7, STN entry date Oct. 14, 2013, Chemical name: Carbamic acid, N-[2-(3-fluorophenyl)ethyl], phenyl ester.
CAS RN: 1329340-85-3, STN entry date Sep. 7, 2011, Chemical name: Carbamic acid, N-[2-[4-(4-morpholinyl)phenyl]ethyl], phenyl ester.
CAS RN: 1582519-57-0, STN entry date Apr. 11, 2014, Chemical name: Benzeneacetamide, 2-amino-N-[2-[1-(4-fluorophenyl)-1H-pyrazol-3-yl]ethyl].
CAS RN: 1088716-89-5, STN entry date Dec. 22, 2008, Chemical name: Benzeneacetamide, N-[2-(1-β-D-ribofuranosyl-1H-imidazol-4-yl)ethyl].
CAS RN: 1583495-90-2, STN entry date Apr. 13, 2014, Chemical name: Benzeneacetamide, 4-amino-N-[2-[4-(2-methyl-4-thiazolyl)phenyl]ethyl].
CAS RN: 1583024-75-2, STN entry date Apr. 12, 2014, Chemical name: Benzenebutanamide, N-(4-aminophenyl)-3-bromo.
CAS RN: 1580673-62-6, STN entry date Apr. 6, 2014, Chemical name: Benzeneacetamide, 2-amino-N-(2-[1,1'-biphenyl]-4-ylethyl).
International Search Report and Written Opinion Issued in International Appln. No. PCT/AU2016/050044, dated Mar. 2, 2016; 13 pages.
Communication issued by the European Patent Office in European Patent Application No. 16 74 2584 dated Jul. 25, 2018, 12 pages total.
Chen, I-L et al., "Aluminium Chloride-Catalyzed Intermolecular vs Intramolecular Friedel-Crafts Reaction of Acrylanilides and 3-Chloropropanamides" Journal of the Chinese Chemical Society (2000) vol. 47, pp. 155-162.

(Continued)

*Primary Examiner* — Samantha L Shterengarts
(74) *Attorney, Agent, or Firm* — Troutman Sanders LLP

(57) ABSTRACT

The present invention relates to new pharmaceutical agents, and to their use in the treatment of proliferative diseases, such as cancer (in particular, brain cancer).

14 Claims, 16 Drawing Sheets

(56) References Cited

OTHER PUBLICATIONS

Den, R.B. et al., "A Phase I Study of the Combination of Sorafenib with Temozolomide and Radiation Therapy for the Treatment of Primary and Recurrent High-Grade Gliomas" International Journal of Radiation: Oncology Biology Physics (2013) vol. 85, No. 2, pp. 321-328.

Fang, X. et al., "Selective Palladium-Catalyzed Aminocarbonylation of Olefins with Aromatic Amines and Nitroarenes" Angewandte Chemie International Edition (2013) vol. 52, No. 52, pp. 14089-14093.

Kher, S. et al., "2-Aryl-N-acyl Indole Derivatives as Liver X Receptor (LXR) Agonists" Bioorganic & Medicinal Chemistry Letters (2007) vol. 17, No. 16, pp. 4442-4446.

Ooguri, A. et al., "Chemi-, Regio- and Stereoselective Preparation of Silyl Enol Ethers from Thiol Esters and Bis(iodozincio)alkane" Chemical Communications (2000) vol. 45, pp. 4761-4763.

Communication issued by the International Searching Authority in International Patent Application No. PCT/AU2016/050044 dated Aug. 1, 2017, 7 pages total.

Communication issued by the State Intellectual Property Office of the People's Republic of China in Chinese Application No. 201680008137.9, dated Jun. 3, 2019, 9 pages total (English translation only).

Communication issued by the European Patent Office in European Patent Application No. 16 74 2584, dated Jun. 28, 2019, 6 pages total.

International Preliminary Report on Patentability issued in International Application No. PCT/AU2016/050044, dated Aug. 1, 2017, 7 pages total.

U87vIII classical subtype

- CMPD1 (EC$_{50}$ = 0.26 ± 0.04 μM)
- cmpd 7 (EC$_{50}$ = 0.78 ± 0.09 μM)
- cmpd 10 (EC$_{50}$ = 2.72 ± 0.5 μM)
- cmpd 13 (EC$_{50}$ = 0.54 ± 0.05 μM)

mesenchymal subtype

- CMPD1 (EC$_{50}$ = 0.91 ± 0.4 μM)
- cmpd 7 (EC$_{50}$ = 2.00 ± 0.3 μM)
- cmpd 10 (EC$_{50}$ = 5.37 ± 1.8 μM)
- cmpd 13 (EC$_{50}$ = 3.82 ± 0.3 μM)

ANTI-CANCER COMPOUNDS

CROSS-REFERENCE TO RELATED APPLICATIONS

This application is a U.S. National Phase of International Patent Application No. PCT/AU2016/050044, filed on Jan. 29, 2016, which published as International Publication No. WO/2016/119017 A1 on Aug. 4, 2016 and claims priority to Australian Patent Application No. 2015900287, filed on Jan. 30, 2015 and Australian Patent Application No. 2015903380, filed on Aug. 20, 2015, all of which applications are herein incorporated by reference in their entirety.

FIELD OF THE INVENTION

The present invention relates to pharmaceutical agents, and to their use in the treatment of proliferative diseases, such as cancer (in particular, brain cancer).

BACKGROUND OF THE INVENTION

Current methods of treating solid cancers of the brain (i.e. brain tumours) involve one or more of surgery, radiation therapy and chemotherapy. For example, glioblastoma (which is the most common brain cancer in humans) is treated using the Stupp protocol. This involves concomitant radiation/temozolomide-based chemotherapy, followed by adjuvant chemotherapy with temozolomide alone, and is carried out after maximal surgical resection of the tumour. Temozolomide prolongs survival by approximately three months (compared to radiation alone) and the median survival of glioblastoma patients is 15 months. Avastin has been approved for recurrent glioblastomas, but has resulted in little improvement in survival.

Further, even though 50% of glioblastomas are dependent on epidermal growth factor receptor (EGFR) signalling, the clinically available EGFR inhibitors have failed in glioblastoma clinical trials. Some inhibitors did not have sufficient Blood-Brain Barrier (BBB) permeability. Recent studies have also revealed that glioblastomas respond only to type II EGFR inhibitors, whereas type I inhibitors were trialled. Extreme heterogeneity and invasiveness of glioblastomas has also contributed to the failure of molecularly-targeted therapies as effective treatments for brain cancers.

Another class of compounds that has been shown to be effective in a number of non-brain cancers are the tubulin-targeting chemotherapeutics. However, the tubulin inhibitors that are clinically used (e.g. Taxol) are very large molecules that are not able to penetrate the BBB. In addition, Taxol and other tubulin-targeting chemotherapeutics (such as vinblastine and vincristine) have serious side effects (e.g. chemotherapy-induced peripheral neuropathy).

Therefore, there is a need to find new treatments for proliferative diseases, such as cancer, and in particular to find effective treatments for brain cancers.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention seeks to address one or more of the above mentioned problems, and/or to provide improvements in cancer therapy and, in a first aspect, provides a compound of formula (I):

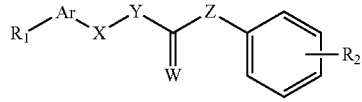

(I)

or a pharmaceutically acceptable salt or prodrug thereof, wherein:
X is $C_1$-$C_6$ alkyl or $C_2$-$C_6$ alkenyl;
Y is $CH_2$, NH, N-alkyl, N-alkenyl, S or O;
W is O, S or NH;
Z is $CH_2$, NH, N-alkyl, N-alkenyl, S or O;
$R_1$ is a halo, cycloalkyl, heterocycloalkyl, aryl or heteroaryl group, which cycloalkyl, heterocycloalkyl, aryl or heteroaryl group is optionally substituted;
Ar is an aryl or heteroaryl group;
$R_2$ is H, OH, $NH_2$ or $NO_2$.

The compound may be a compound of formula (I):

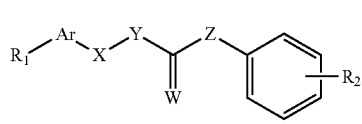

(I)

or a pharmaceutically acceptable salt or prodrug thereof, wherein:
X is $C_1$-$C_6$ alkyl or $C_2$-$C_6$ alkenyl;
Y is $CH_2$, NH, N-alkyl, N-alkenyl, S or O;
W is O, S or NH;
Z is $CH_2$, NH, N-alkyl, N-alkenyl, S or O;
$R_1$ is a halo, cycloalkyl, heterocycloalkyl, aryl or heteroaryl group, which cycloalkyl, heterocycloalkyl, aryl or heteroaryl group is optionally substituted;
Ar is an aryl or heteroaryl group;
$R_2$ is H, OH, $NH_2$ or $NO_2$,
provided that the compound does not have the following structure:

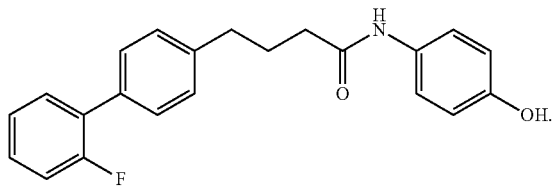 [SMILES: O=C(CCCc1ccc(-c2ccccc2F)cc1)Nc1ccc(O)cc1]

The compound may be a compound of formula (I):

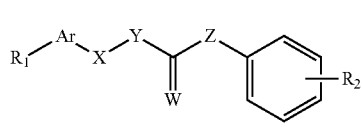

(I)

or a pharmaceutically acceptable salt or prodrug thereof, wherein:
X is $C_1$-$C_6$ alkyl or $C_2$-$C_6$ alkenyl;
Y is $CH_2$, NH, N-alkyl, N-alkenyl, S or O;
W is O, S or NH;
Z is $CH_2$, NH, N-alkyl, N-alkenyl, S or O;

$R_1$ is a halo, cycloalkyl, heterocycloalkyl, aryl or heteroaryl group, which cycloalkyl, heterocycloalkyl, aryl or heteroaryl group is optionally substituted;

Ar is an aryl or heteroaryl group;

$R_2$ is H, OH, $NH_2$ or $NO_2$, provided that when $R_1$ is aryl (particularly phenyl), $R_1$ is not substituted by F.

X may be $C_2$ alkyl or $C_2$ alkenyl.

Y may be $CH_2$. Z may be NH. Z may be O. Z may be $CH_2$.

Y may be NH. Y may be O.

Both Y and Z may be NH.

Y may be $CH_2$ and Z may be NH.

Z may be $CH_2$ and Y may be NH.

Y may be $CH_2$ and Z may be O.

Y may be O and Z may be $CH_2$.

W may be O.

$R_1$ may be a halo group (e.g. Br). $R_1$ may be an aryl group. The aryl group may be monocyclic or bicyclic. The aryl group may be phenyl or naphthyl.

The aryl group may be substituted. The substituent may be selected from a halo group and a heteroalkyl group. The halo group may be F, the heteroalkyl group may be O-alkyl (e.g. $-OCH_3$) or aminoalkyl (e.g. $-CH_2NH_2$).

$R_1$ may be a heteroaryl group. The heteroaryl group may be monocyclic or bicyclic. The heteroaryl group may include one or more nitrogen atoms. For example, the heteroaryl group may be pyrazole, isoxazole, triazole, pyridine, pyrimidine, quinoline, benzimidazole or indole. The heteroaryl group may be substituted. For example, the substituent may be a halo group (e.g. F) or a heteroalkyl group (e.g. O-alkyl, such as $-OCH_3$, or aminoalkyl, such as $-CH_2NH_2$).

$R_1$ may be a heterocycloalkyl group. The heterocycloalkyl group may include one or more nitrogen atoms. The heterocycloalkyl group may be piperazine. The heterocycloalkyl group may include one or more oxygen atoms (in addition to, or as an alternative to, one or more nitrogen atoms). The heterocycloalkyl group may be morpholine. The heterocycloalkyl group may be substituted by, for example, a halo group (e.g. F) or a heteroalkyl group (e.g. O-alkyl, such as $-OCH_3$, or aminoalkyl, such as $-CH_2NH_2$).

Ar may be an aryl group. The aryl group may be phenyl. In one embodiment, Ar is a heteroaryl group. The heteroaryl group may include one or more nitrogen atoms and/or NH groups. The heteroaryl group may have 4 or 5 ring carbon atoms. The heteroaryl group could be pyridine or pyrimidine.

$R_2$ may be H or OH. $R_2$ may be at the para position.

The compound of formula (I) may be selected from:

SC-38

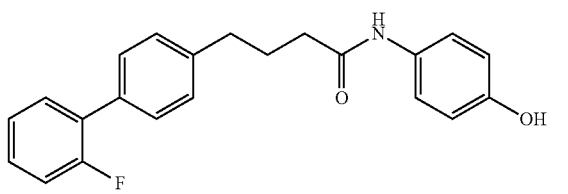 [SMILES: O=C(CCCc1ccc(-c2ccccc2F)cc1)Nc1ccc(O)cc1]

1-01

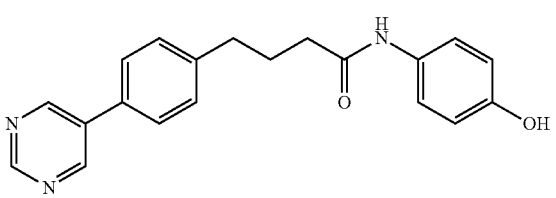

1-07

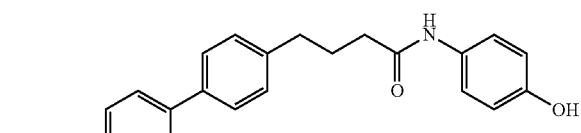

1-08

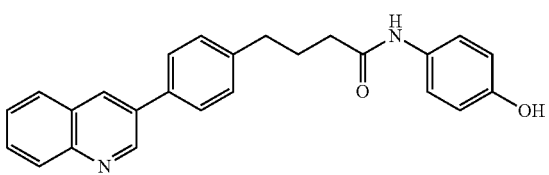

1-17

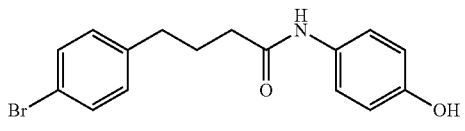

1-18

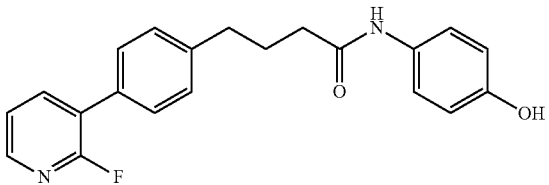

1-19

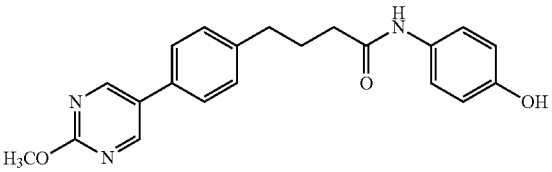

1-20

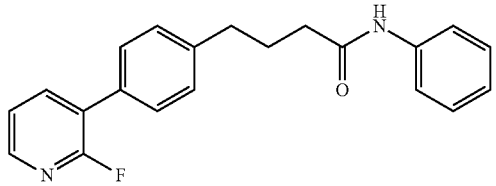

1-21

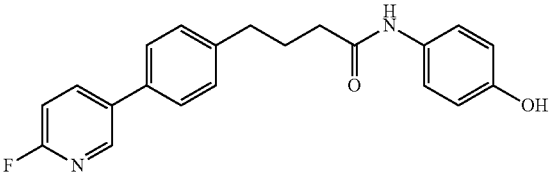

1-22

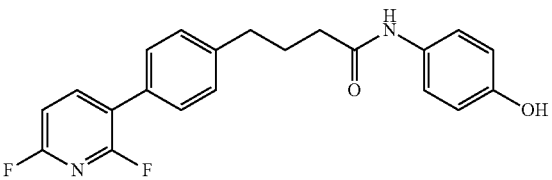

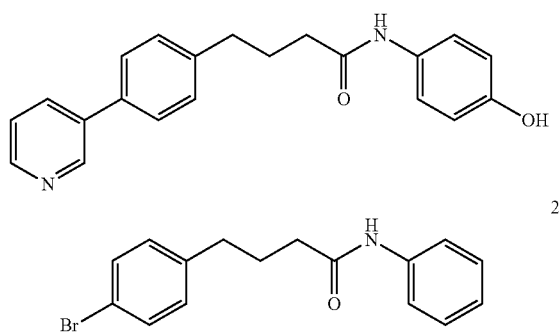

The compound of formula (I) may be selected from:
4-(4-bromophenyl)-N-(4-hydroxyphenyl)butanamide
4-(4-(2-fluoropyridin-3-yl)phenyl)-N-(4-hydroxyphenyl)butanamide
4-(4-(2,6-difluoropyridin-3-yl)phenyl)-N-(4-hydroxyphenyl)butanamide
4-(4-(6-fluoropyridin-3-yl)phenyl)-N-(4-hydroxyphenyl)butanamide
N-(4-hydroxyphenyl)-4-(4-(pyridin-3-yl)phenyl)butanamide
N-(4-hydroxyphenyl)-4-(4-(2-methoxypyrimidin-5-yl)phenyl)butanamide
4-(4-bromophenyl)-N-phenylbutanamide
4-(4-(2-fluoropyridin-3-yl)phenyl)-N-phenylbutanamide
N-(4-hydroxyphenyl)-4-(4-(pyrimidin-5-yl)phenyl)butanamide
4-(4'-(aminomethyl)-[1,1'-biphenyl]-4-yl)-N-(4-hydroxyphenyl)butanamide
N-(4-hydroxyphenyl)-4-(4-(quinolin-3-yl)phenyl)butanamide.

In a second aspect, the present invention relates to a pharmaceutical composition including a compound of formula (I) (according to the first aspect of the invention) together with a pharmaceutically acceptable carrier, diluent or excipient.

Compounds and pharmaceutical compositions according to the present invention may be suitable for the treatment or prevention of a proliferative disease. Accordingly, in another aspect, the present invention relates to a method of treating or preventing a proliferative disease in a subject, the method including administering to the subject an effective amount of a compound of formula (I) according to the first aspect of the invention or a pharmaceutical composition according to the second aspect of the invention.

In a further aspect the present invention relates to the use of a compound of formula (I) according to the first aspect of the invention or a pharmaceutical composition according to the second aspect of the invention in the manufacture of a medicament for treating or preventing a proliferative disease.

In a further aspect the present invention relates to the use of a compound of formula (I) according to the first aspect of the invention or a pharmaceutical composition according to the second aspect of the invention for the treatment or prevention of a proliferative disease in a subject.

In a further aspect the present invention relates to a compound of formula (I) according to the first aspect of the invention or a pharmaceutical composition according to the second aspect of the invention for use in the treatment or prevention of a proliferative disease in a subject.

In one embodiment, the proliferative disease is cancer. The cancer may be selected from the group consisting of brain cancer, breast cancer, lung cancer, prostate cancer, ovarian cancer, uterine cancer, skin cancer, colon cancer and bladder cancer.

The cancer may be primary. The cancer may be metastatic. The cancer may be benign. The cancer may be malignant.

The cancer may be brain cancer (e.g. anaplastic astrocytoma, astrocytoma, central neurocytoma, choroid plexus carcinoma, choroid plexus papilloma, choroid plexus tumour, diffuse intrinsic pontine glioma, dysembryoplastic neuroepithelial tumour, ependymal tumour, fibrillary astrocytoma, giant-cell glioblastoma, glioblastoma multiforme, gliomatosis cerebri, gliosarcoma, hemangiopericytoma, medulloblastoma, medulloepithelioma, meningeal carcinomatosis, neuroblastoma, neurocytoma, oligoastrocytoma, oligodendroglioma, optic nerve sheath meningioma, pediatric ependymoma, pilocytic astrocytoma, pinealoblastoma, pineocytoma, pleomorphic anaplastic neuroblastoma, pleomorphic xanthoastrocytoma, primary central nervous system lymphoma, sphenoid wing meningioma, subependymal giant cell astrocytoma, subependymoma, trilateral retinoblastoma). The brain cancer may be a primary cancer (e.g. a glioma, a meningioma, a pituitary adenoma or a nerve sheath tumour). The brain cancer may be a metastatic cancer (e.g. a result of melanoma or lung cancer).

In a further aspect, the present invention relates to a method of completely or partially preventing the recurrence of a solid tumour in a subject, the method including administering to the subject an effective amount of a compound of formula (I) according to the first aspect of the invention or a pharmaceutical composition according to the second aspect of the invention.

In another aspect the invention relates to the use of a compound according to the first aspect of the invention or the pharmaceutical composition according to the second aspect of the invention in the manufacture of a medicament for completely or partially preventing the recurrence of a solid tumour.

In a further aspect the present invention relates to the use of a compound of formula (I) according to the first aspect of the invention or a pharmaceutical composition according to the second aspect of the invention for completely or partially preventing the recurrence of a solid tumour in a subject.

In a further aspect the present invention relates to a compound of formula (I) according to the first aspect of the invention or a pharmaceutical composition according to the second aspect of the invention for use in completely or partially preventing the recurrence of a solid tumour in a subject.

The solid tumour may be a brain cancer (e.g. glioblastoma, astrocytoma, or glioma). The brain cancer may be a primary cancer. The brain cancer may be a metastatic cancer.

The compounds of formula (I) may be used in therapy alone or in combination with one or more other therapeutic agents, for example, as part of a combination therapy.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1A:
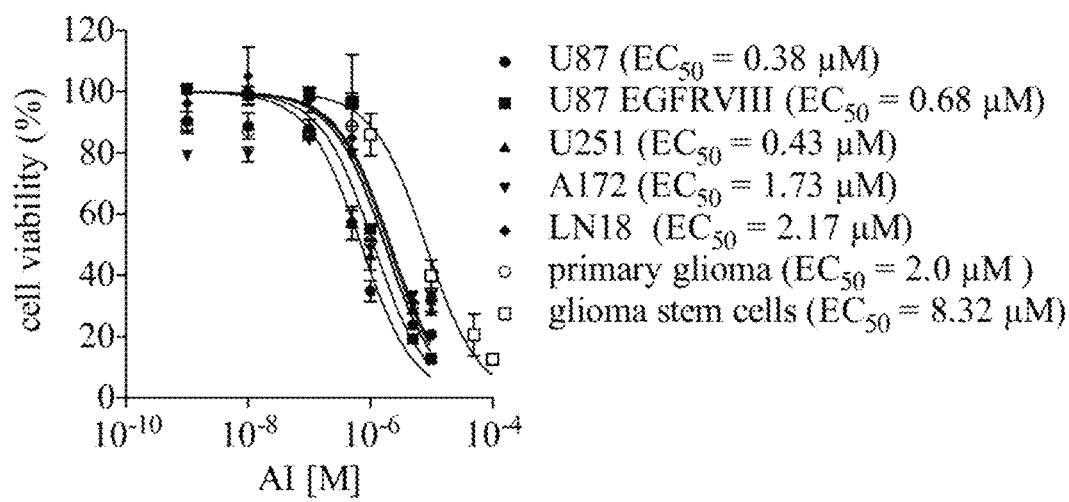
FIGS. 1A-1B. Results of treatment of various cancer cell lines with SC-38 to test cancer cell viability (1A) and cytotoxicity (1B) of SC-38.

The invention is based on the surprising finding that compounds of formula (I) provide unexpected improvement in the treatment of proliferative diseases, such as cancer, and especially brain cancers.

Compounds are generally described herein using standard nomenclature. For compounds having asymmetric centres, it will be understood that, unless otherwise specified, all of the optical isomers and mixtures thereof are encompassed. Compounds with two or more asymmetric elements can also be present as mixtures of diastereomers. In addition, compounds with carbon-carbon double bonds may occur in Z and E forms, with all isomeric forms of the compounds being included in the present invention unless otherwise specified. Where a compound exists in various tautomeric forms, a recited compound is not limited to any one specific tautomer, but rather is intended to encompass all tautomeric forms. Recited compounds are further intended to encompass compounds in which one or more atoms are replaced with an isotope, i.e., an atom having the same atomic number but a different mass number. By way of general example, and without limitation, isotopes of hydrogen include tritium and deuterium and isotopes of carbon include $^{11}C$, $^{13}C$, and $^{14}C$.

Compounds according to the formula provided herein, which have one or more stereogenic centres, have an enantiomeric excess of at least 50%. For example, such compounds may have an enantiomeric excess of at least 60%, 70%, 80%, 85%, 90%, 95%, or 98%. Some embodiments of the compounds have an enantiomeric excess of at least 99%. It will be apparent that single enantiomers (optically active forms) can be obtained by asymmetric synthesis, synthesis from optically pure precursors, biosynthesis or by resolution of the racemates, for example, enzymatic resolution or resolution by conventional methods such as crystallization in the presence of a resolving agent, or chromatography, using, for example, a chiral HPLC column.

Certain compounds are described herein using a general formula that includes variables such as $R_1$, $R_2$, Ar, W, X, Y and Z. Unless otherwise specified, each variable within such a formula is defined independently of any other variable, and any variable that occurs more than one time in a formula is defined independently at each occurrence. Therefore, for example, if a group is shown to be substituted with 0, 1 or 2 R*, the group may be unsubstituted or substituted with up to two R* groups and R* at each occurrence is selected independently from the definition of R*. Also, combinations of substituents and/or variables are permissible only if such combinations result in stable compounds, i.e., compounds that can be isolated, characterized and tested for biological activity.

A "pharmaceutically acceptable salt" of a compound disclosed herein is an acid or base salt that is generally considered in the art to be suitable for use in contact with the tissues of human beings or animals without excessive toxicity or carcinogenicity, and preferably without irritation, allergic response, or other problem or complication. In particular, pharmaceutically acceptable salts in accordance with the present invention are those that do not adversely affect the ability of the compound to cross the BBB. Such salts include mineral and organic acid salts of basic residues such as amines, as well as alkali or organic salts of acidic residues such as carboxylic acids.

Suitable pharmaceutically acceptable salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzenesulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic (such as acetic, HOOC—$(CH_2)_n$—COOH where n is any integer from 0 to 6, i.e. 0, 1, 2, 3, 4, 5 or 6), and the like. Similarly, pharmaceutically acceptable cations include, but are not limited to sodium, potassium, calcium, aluminum, lithium and ammonium. A person skilled in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent (such as ether, ethyl acetate, ethanol, iso-propanol or acetonitrile), or in a mixture of the two.

It will be apparent that each compound of formula (I) may, but need not, be present as a hydrate, solvate or non-covalent complex. In addition, the various crystal forms and polymorphs are within the scope of the present invention, as are prodrugs of the compounds of formula (I) provided herein.

A "prodrug" is a compound that may not fully satisfy the structural requirements of the compounds provided herein, but is modified in vivo, following administration to a subject or patient, to produce a compound of formula (I) provided herein. For example, a prodrug may be an acylated derivative of a compound as provided herein. Prodrugs include compounds wherein hydroxy, carboxy, amine or sulfhydryl groups are bonded to any group that, when administered to a mammalian subject, cleaves to form a free hydroxy, carboxy, amino, or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to generate the parent compounds.

A "substituent" as used herein, refers to a molecular moiety that is covalently bonded to an atom within a molecule of interest. For example, a "ring substituent" may be a moiety such as a halogen, alkyl group, heteroalkyl group, haloalkyl group or other substituent described herein that is covalently bonded to an atom, preferably a carbon or nitrogen atom, that is a ring member. The term "substituted," as used herein, means that any one or more hydrogens on the designated atom is replaced with a selection from the indicated substituents, provided that the designated atom's normal valence is not exceeded, and that the substitution results in a stable compound, i.e., a compound that can be isolated, characterized and tested for biological activity. When a substituent is oxo, i.e., =O, then two hydrogens on the atom are replaced. An oxo group that is a substituent of an aromatic carbon atom results in a conversion of —CH— to —C(=O)— and a loss of aromaticity. For example a pyridyl group substituted by oxo is a pyridone. Examples of suitable substituents are alkyl (including haloalkyl e.g. $CF_3$), heteroalkyl (e.g. —$OCH_3$, —$CH_2NHCH_3$, —$CH_2NH_2$), halogen (for example, fluorine, chlorine, bromine or iodine atoms), OH, =O, SH, $SO_3H$, $NH_2$, =NH, $N_3$ and $NO_2$ groups.

The term "alkyl" refers to a saturated, straight-chain or branched hydrocarbon group. Specific examples of alkyl groups are methyl, ethyl, propyl, iso-propyl, n-butyl, iso-butyl, sec-butyl, tert-butyl, n-pentyl, iso-pentyl, n-hexyl and 2,2-dimethylbutyl.

The term "heteroalkyl" refers to an alkyl group as defined above that contains one or more heteroatoms selected from oxygen, nitrogen and sulphur (especially oxygen and nitrogen). Specific examples of heteroalkyl groups are O-alkyl groups, such as methoxy, trifluoromethoxy, ethoxy, n-propyloxy, iso-propyloxy, butoxy and tert-butyloxy, methoxymethyl, ethoxymethyl, —$CH_2CH_2OH$, —$CH_2OH$, methoxyethyl, 1-methoxyethyl, 1-ethoxyethyl, 2-methoxyethyl or 2-ethoxyethyl, aminoalkyl (such as —$CH_2NH_2$, —$CH_2CH_2NH_2$, etc) methylamino, ethylamino, propylamino, iso-propylamino, dimethylamino, diethylamino, iso-propylethylamino, methylamino methyl, ethylamino methyl, di-iso-propylamino ethyl, methylthio, ethylthio, iso-propylthio, enol ether, dimethylamino methyl, dimethylamino ethyl, acetyl, propionyl, butyryloxy, acetyloxy, methoxycarbonyl, ethoxycarbonyl, propionyloxy, acetylamino, propionylamino, carboxymethyl, carboxyethyl, carboxypropyl, N-ethyl-N-methylcarbamoyl and N-methylcarbamoyl. Further examples of heteroalkyl groups are nitrile, iso-nitrile, cyanate, thiocyanate, iso-cyanate, iso-thiocyanate and alkylnitrile groups.

The term "alkenyl" refers to an at least partially unsaturated, straight-chain or branched hydrocarbon group that contains at least two carbon atoms (i.e. $C_2$ alkenyl). Specific examples of alkenyl groups are ethenyl (vinyl), propenyl (allyl), iso-propenyl, butenyl, ethinyl, propinyl, butinyl, acetylenyl, propargyl, iso-prenyl and hex-2-enyl group. Preferably, alkenyl groups have one or two double bond(s).

The term "cycloalkyl" refers to a saturated or partially unsaturated (for example, a cycloalkenyl group) cyclic group that contains one or more rings (preferably 1 or 2), and contains from 3 to 14 ring carbon atoms, preferably from 3 to 10 (especially 3, 4, 5, 6 or 7) ring carbon atoms. Specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0] nonyl, tetraline, adamantane (i.e. tricycle[3.3.1.13,7]decane), cyclopentylcyclohexyl and cyclohex-2-enyl.

The term "heterocycloalkyl" refers to a cycloalkyl group as defined above in which one or more (preferably 1, 2 or 3) ring carbon atoms, each independently, have been replaced by an oxygen, nitrogen, silicon, selenium, phosphorus or sulfur atom (preferably by an oxygen, sulfur or nitrogen atom). This includes groups containing these atoms, such as NH. A heterocycloalkyl group has preferably 1 or 2 rings containing from 3 to 10 (especially 3, 4, 5, 6 or 7) ring atoms (preferably selected from C, O, N and S). Specific examples are piperidyl, prolinyl, imidazolidinyl, piperazinyl, morpholinyl, urotropinyl, pyrrolidinyl, tetrahydrothiophenyl, tetrahydropyranyl, tetrahydrofuryl and 2-pyrazolinyl group and also lactames, lactones, cyclic imides and cyclic anhydrides.

The term "aryl" refers to an aromatic group that contains one or more rings containing from 6 to 14 ring carbon atoms, preferably from 6 to 10 (especially 6) ring carbon atoms. Examples are phenyl, naphthyl and biphenyl groups.

The term "heteroaryl" refers to an aromatic group that contains one or more rings containing from 5 to 14 ring atoms, preferably from 5 to 10 (especially 5 or 6) ring atoms, and contains one or more (preferably 1, 2, 3 or 4) oxygen, nitrogen, phosphorus or sulfur ring atoms (preferably O, S or N). This includes O, S or N-containing groups, such as NH. Examples are pyridyl (for example, 4-pyridyl), imidazolyl (for example, 2-imidazolyl), phenylpyrrolyl (for example, 3-phenylpyrrolyl), thiazolyl, iso-thiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, iso-quinolinyl, pyrrolyl, purinyl, carbazolyl, acridinyl, pyrimidyl, 2,3'-bifuryl and pyrazolyl (for example, 3-pyrazolyl) groups.

The expression "halogen" or "halogen atom" as used herein means fluorine, chlorine, bromine, or iodine.

The term "optionally substituted" refers to a group in which one, two, three or more hydrogen atoms have been replaced independently of each other by halogen (for example, fluorine, chlorine, bromine or iodine atoms) and/or by, for example, OH, =O, SH, $SO_3H$, $NH_2$, N-alkyl, NH-alkyl, $N_3$ or $NO_2$ groups. This expression also refers to a group that is substituted by one, two, three or more alkyl, alkenyl or heteroalkyl (e.g. —$OCH_3$, —$OCH_2CH_3$, —$CH_2NHCH_3$ and —$CH_2NH_2$) groups. These groups may themselves be substituted. For example, an alkyl group substituent may be substituted by one or more halogen atoms (i.e. may be a haloalkyl group). The term "haloalkyl" refers to an alkyl group (as defined above) that is substituted by one or more halogen atoms (as also defined above).

Specific examples of haloalkyl groups are trifluoromethyl, dichloroethyl, dichloromethyl and iodoethyl.

As used herein a wording defining the limits of a range of length such as, for example, "from 1 to 5" means any integer from 1 to 5, i.e. 1, 2, 3, 4 and 5. In other words, any range defined by two integers explicitly mentioned is meant to comprise and disclose any integer defining said limits and any integer comprised in said range.

Preferred compounds of formula (I) are those where X is $C_1$, $C_2$ or $C_3$ alkyl, or $C_2$ or $C_3$ alkenyl (e.g. $C_2$ alkyl or $C_2$ alkenyl). X may also be $C_1$ alkyl.

Y may be $CH_2$. Z may be NH. Z may be O. Z may be $CH_2$.
Y may be NH. Y may be O.
Both Y and Z may be NH.
Y may be $CH_2$ and Z may be NH.
Z may be $CH_2$ and Y may be NH.
Y may be $CH_2$ and Z may be O.
Y may be O and Z may be $CH_2$.

$R_1$ may be a halo group (e.g. Br). $R_1$ may be an aryl group. The aryl group may be monocyclic or bicyclic. The aryl group may be phenyl or naphthyl.

The aryl group may be substituted. The substituent may be selected from a halo group and a heteroalkyl group. The halo group may be F, and the heteroalkyl group may be O-alkyl (e.g. $OCH_3$ or $OCH_2CH_3$) or aminoalkyl (e.g. —$CH_2NH_2$ or —$CH_2CH_2NH_2$).

$R_1$ may be a heteroaryl group. The heteroaryl group may be monocyclic or bicyclic. The heteroaryl group may include one or more nitrogen atoms. For example, the heteroaryl group may be pyrazole, isoxazole, triazole, pyridine, pyrimidine, quinoline, benzimidazole or indole. The heteroaryl group may be substituted. For example, the substituent may be a halo group (e.g. F) or a heteroalkyl group (e.g. O-alkyl, such as —$OCH_3$ or $OCH_2CH_3$, or aminoalkyl, such as —$CH_2NH_2$ or —$CH_2CH_2NH_2$).

$R_1$ may be a heterocycloalkyl group. The heterocycloalkyl group may include one or more nitrogen atoms. The heterocycloalkyl group may be piperazine. The heterocycloalkyl group may include one or more oxygen atoms. The heterocycloalkyl group may be morpholine. The heterocycloalkyl group may be substituted by, for example, a halo group (e.g. F) or a heteroalkyl group (e.g. O-alkyl, such as —$OCH_3$ or $OCH_2CH_3$, or aminoalkyl, such as e.g. —$CH_2NH_2$ or —$CH_2CH_2NH_2$).

Ar may be an aryl group. The aryl group may be phenyl. Ar may be a heteroaryl group. The heteroaryl group may include one or more nitrogen atoms. The heteroaryl group may have 4 or 5 ring carbon atoms. The heteroaryl group may be pyridine or pyrimidine.

$R_2$ may be H or OH. $R_2$ may be at the para position.

Specific examples of the compounds of the present invention are given in Table 1, below.

TABLE 1

Examples of compounds of the present invention

| Compound | Structure |
|---|---|
| SC-38 | 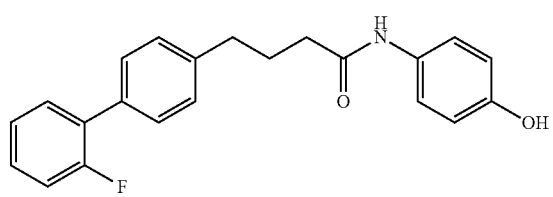 |

TABLE 1-continued

Examples of compounds of the present invention

| Compound | Structure |
|---|---|
| 1-01 | 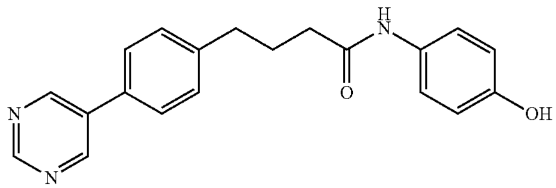 [SMILES: O=C(CCCc1ccc(-c2cncnc2)cc1)Nc1ccc(O)cc1] |
| 1-07 | 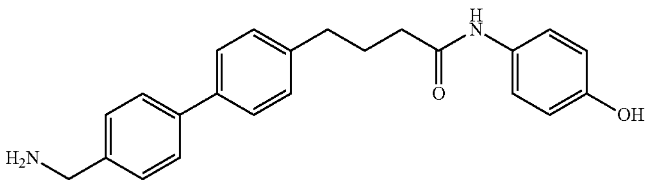 [SMILES: NCc1ccc(-c2ccc(CCCC(=O)Nc3ccc(O)cc3)cc2)cc1] |
| 1-08 | 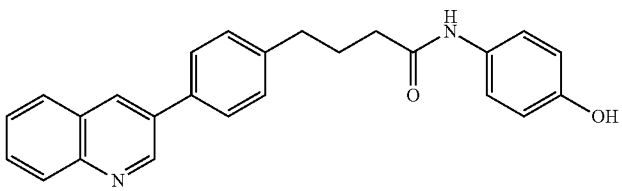 [SMILES: O=C(CCCc1ccc(-c2cnc3ccccc3c2)cc1)Nc1ccc(O)cc1] |
| 1-17 | 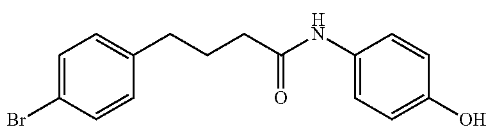 [SMILES: O=C(CCCc1ccc(Br)cc1)Nc1ccc(O)cc1] |
| 1-18 | 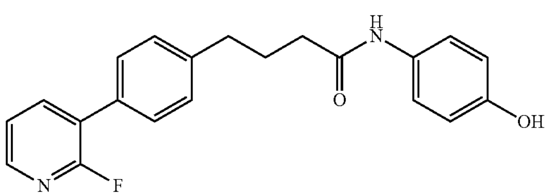 [SMILES: O=C(CCCc1ccc(-c2cccnc2F)cc1)Nc1ccc(O)cc1] |
| 1-19 | 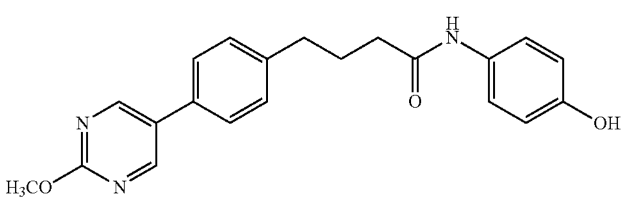 [SMILES: COc1ncc(-c2ccc(CCCC(=O)Nc3ccc(O)cc3)cc2)cn1] |
| 1-20 | 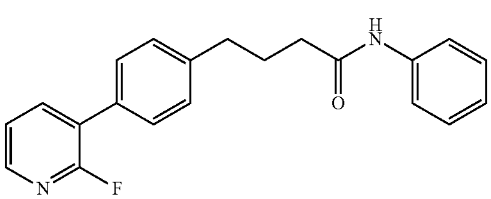 [SMILES: O=C(CCCc1ccc(-c2cccnc2F)cc1)Nc1ccccc1] |
| 1-21 | 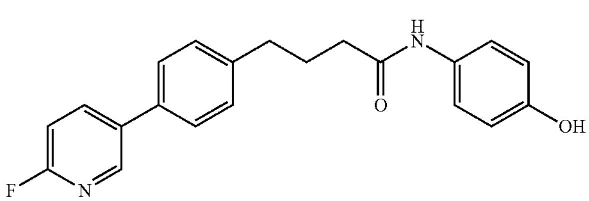 [SMILES: O=C(CCCc1ccc(-c2ccc(F)nc2)cc1)Nc1ccc(O)cc1] |

TABLE 1-continued

Examples of compounds of the present invention

| Compound | Structure |
|---|---|
| 1-22 | 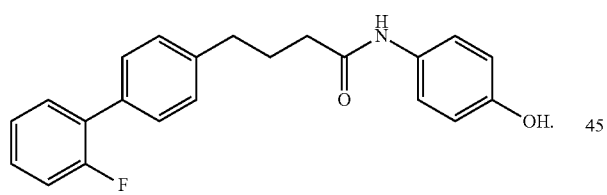 |
| 1-38 | 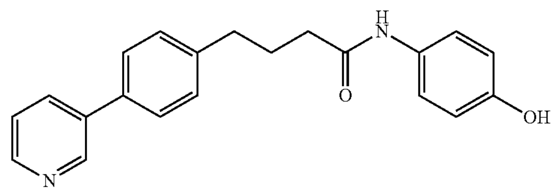 [SMILES: O=C(CCCc1ccc(-c2cccnc2)cc1)Nc1ccc(O)cc1] |
| 20 | 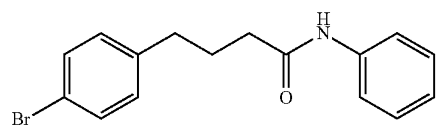 [SMILES: O=C(CCCc1ccc(Br)cc1)Nc1ccccc1] |

In one embodiment, the compound of formula (I) is selected from the group consisting of compounds 1-01, 1-07, 1-08, 1-17, 1-18, 1-19, 1-20, 1-21, 1-22, 1-38 and 20 from Table 1 above.

In another embodiment, the compound of formula (I) does not include compound SC-38 from Table 1 above.

In one embodiment, the compound of the present invention is a compound of formula (I), as described herein, provided that the compound does not have the following structure:

In one embodiment, the compound of the present invention is a compound of formula (I), as described herein, provided that when $R_1$ is aryl (particularly phenyl), $R_1$ is not substituted by F.

The compounds of the present invention can be synthesised by any suitable method known to a person skilled in the art. A general synthesis is given below in Scheme 1.

Scheme 1. Example of a general synthesis of the compounds of the present invention

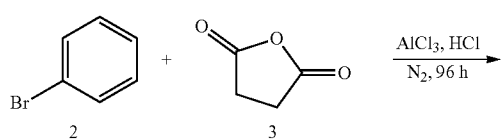

The compounds of the present invention may exhibit high anti-proliferative activity and in particular, high efficacy against brain cancers. Specifically, in the examples herein, specific compounds are shown to induce apoptosis and are also able to cross the BBB.

The therapeutic use of compounds of formula (I), their pharmaceutically acceptable salts, solvates, hydrates, prodrugs and also formulations and pharmaceutical compositions (including mixtures of the compounds of formula (I)) are within the scope of the present invention. Accordingly, the present invention also relates to pharmaceutical compositions including a therapeutically effective amount of a compound of formula (I), or its pharmaceutically acceptable salt, solvate, hydrate or prodrug, and one or more pharmaceutically acceptable excipients.

A "pharmaceutical carrier, diluent or excipient" includes, but is not limited to, any physiological buffered (i.e., about pH 7.0 to 7.4) medium including a suitable water soluble carrier, conventional solvents, dispersion media, fillers, solid carriers, coatings, antibacterial and antifungal agents, isotonic and absorption delaying agents. Suitable water soluble carriers include, but are not limited to saline, dextrose, corn oil, dimethylsulfoxide, and gelatin capsules. Other conventional additives include lactose, mannitol, corn starch, potato starch, binders such as crystalline cellulose, cellulose derivatives, acacia, gelatins, disintegrators such as sodium carboxymethyl-cellulose, and lubricants such as talc or magnesium stearate.

Pharmaceutical compositions may be formulated for any appropriate route of administration including, for example, topical (for example, transdermal or ocular), oral, buccal, nasal, vaginal, rectal or parenteral administration. The term "parenteral" as used herein includes subcutaneous, intradermal, intravascular (for example, intravenous), intramuscular, spinal, intracranial, intrathecal, intraocular, periocular, intraorbital, intrasynovial and intraperitoneal injection, as well as any similar injection or infusion technique. In certain embodiments, compositions in a form suitable for oral use or parenteral use are preferred. Suitable oral forms include, for example, tablets, troches, lozenges, aqueous or oily suspensions, dispersible powders or granules, emulsions, hard or soft capsules, or syrups or elixirs. For intravenous, intramuscular, subcutaneous, or intraperitoneal administration, one or more compounds may be combined with a sterile aqueous solution which is preferably isotonic with the blood of the recipient. Such formulations may be prepared by dissolving solid active ingredient in water containing physiologically compatible substances such as sodium chloride or glycine, and having a buffered pH compatible with physiological conditions to produce an aqueous solution, and rendering said solution sterile. The formulations may be present in unit or multi-dose containers such as sealed ampoules or vials. Examples of suitable components are described in Martindale—The Extra Pharmacopoeia (Pharmaceutical Press, London 1993) and Martin (ed.), Remington's Pharmaceutical Sciences.

For the treatment of proliferative disorders, the dose of the biologically-active compound according to the invention may vary within wide limits and may be adjusted to individual requirements. Active compounds according to the present invention are generally administered in a therapeutically effective amount. Preferred doses range from about 0.1 mg to about 140 mg per kilogram of body weight per day (e.g. about 0.5 mg to about 7 g per patient per day). The daily dose may be administered as a single dose or in a plurality of doses. The amount of active ingredient that may be combined with the carrier materials to produce a single dosage form will vary depending upon the host treated and the particular mode of administration. Dosage unit forms will generally contain between about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination (i.e. other drugs being used to treat the patient), the severity of the particular disorder undergoing therapy, and the location of the unwanted proliferating cells. The dosage will generally be lower if the compounds are administered locally rather than systemically, and for prevention rather than for treatment. Such treatments may be administered as often as necessary and for the period of time judged necessary by the treating physician. A person skilled in the art will appreciate that the dosage regime or therapeutically effective amount of the compound of formula (I) to be administered may need to be optimized for each individual.

It will be appreciated that different dosages may be required for treating different disorders. An effective amount of an agent is that amount which causes a statistically significant decrease in neoplastic cell count, growth or size. Neoplastic disorders responsive to the agents of the present invention include, but are not limited to, brain cancer.

The terms "therapeutically effective amount" or "effective amount" refer to an amount of the compound of formula (I) that results in prevention, an improvement or remediation of the symptoms of a proliferative disorder. The dosage form and amount of the compounds or pharmaceutical compositions of the present invention can be readily established by reference to known treatment or prophylactic regimens.

Preferred compounds of the invention will have certain pharmacological properties. Such properties include, but are not limited to oral bioavailability and BBB permeability, such that the preferred oral dosage forms discussed above can provide therapeutically effective levels of the compound in vivo.

The compounds of the present invention are preferably administered to a patient (for example, a human) orally or parenterally, and are present within at least one body fluid or tissue of the patient. Accordingly, the present invention further provides methods for treating patients suffering from proliferative disorders (including cancer, such as brain cancer).

The terms "treating", "treatment" and "therapy" are used herein to refer to curative therapy. Therefore, in the context of the present disclosure, the term "treating" encompasses curing and ameliorating the severity of cancer or its associated symptoms.

"Preventing" or "prevention" means preventing the occurrence of the cancer or tempering the severity of the cancer if it develops subsequent to the administration of the compounds or pharmaceutical compositions of the present invention. This prevents the onset of clinically evident unwanted cell proliferation altogether or the onset of a preclinically evident stage of unwanted rapid cell proliferation in individuals at risk.

Patients may include but are not limited to primates, especially humans, domesticated companion animals such as dogs, cats, horses, and livestock such as cattle, pigs, sheep, with dosages as described herein.

Compounds of the present invention may be useful for the treatment and/or prevention of conditions and disorders associated with cell proliferation (including cancer, such as brain cancer). Accordingly, the present invention also relates to a method of treating or preventing a proliferative disorder in a patient including administration to the patient of a therapeutically effective amount of a compound of formula (I), or a pharmaceutically-acceptable salt, solvate, hydrate or prodrug thereof. The present invention also relates to the use of a therapeutically effective amount of a compound of formula (I), or a pharmaceutically-acceptable salt, solvate, hydrate or prodrug thereof, for treating or preventing a proliferative disorder. The present invention also provides a pharmaceutical composition for use in treating or preventing a proliferative disorder, in any of the embodiments described in the specification. The present invention also relates to the use of a therapeutically effective amount of a compound of formula (I), or a pharmaceutically acceptable salt, solvate, hydrate or prodrug thereof, for the manufacture of a medicament for treating or preventing a proliferative disorder.

The present invention also relates to a compound of formula (I), or a pharmaceutically acceptable salt, solvate, hydrate or prodrug thereof, when used in a method of treating or preventing a proliferative disorder. The present invention also relates to a composition having an active ingredient for use in treating or preventing a proliferative disorder, wherein the active ingredient is a compound of formula (I), or a pharmaceutically acceptable salt, solvate, hydrate or prodrug thereof. The present invention also relates to the use of a pharmaceutical composition containing a compound of the formula (I), or a pharmaceutically acceptable salt, solvate, hydrate or prodrug thereof, in treating or preventing a proliferative disorder, such as described above. In one embodiment, the compound of formula (I) is essentially the only active ingredient of the composition. In one embodiment, the proliferative disorder is a cancer. In one embodiment, the cancer is a brain cancer (e.g. a solid tumour).

The compounds of formula (I) according to the present invention, and pharmaceutical compositions thereof, may be used in the treatment or prevention of proliferative diseases, preferably cancer. The compounds and compositions of the invention may be useful for the treatment of a wide variety of cancers (tumours), including but not limited to, solid tumours, such as for example, brain cancer, breast cancer, lung cancer, prostate cancer, ovarian cancer, uterine cancer brain cancer, skin cancer, colon cancer and bladder cancer.

The type of cancer or tumor cells that may be amenable to treatment according to the invention include, for example, breast, colon, lung, and prostate cancers, gastrointestinal cancers including esophageal cancer, stomach cancer, colorectal cancer, polyps associated with colorectal neoplasms, pancreatic cancer and gallbladder cancer, cancer of the adrenal cortex, ACTH-producing tumor, bladder cancer, brain cancer (including those discussed below), Ewing's sarcoma, head and neck cancer including mouth cancer and larynx cancer, kidney cancer including renal cell carcinoma, liver cancer, lung cancer including small and non-small cell lung cancers, malignant peritoneal effusion, malignant pleural effusion, skin cancers including malignant melanoma, tumor progression of human skin keratinocytes, squamous cell carcinoma, basal cell carcinoma, and hemangiopericytoma, mesothelioma, Kaposi's sarcoma, bone cancer including osteomas and sarcomas such as fibrosarcoma and osteosarcoma, cancers of the female reproductive tract including uterine cancer, endometrial cancer, ovarian cancer, ovarian (germ cell) cancer and solid tumors in the ovarian follicle, vaginal cancer, cancer of the vulva, and cervical cancer, breast cancer (small cell and ductal), penile cancer, retinoblastoma, testicular cancer, thyroid cancer, trophoblastic neoplasms, and Wilms' tumor. In one embodiment, the cancer is primary. In one embodiment, the cancer is metastatic. In one embodiment, the cancer is benign. In one embodiment, the cancer is malignant.

In one embodiment, the proliferative disorder to be treated and/or prevented is brain cancer. The brain cancer may be selected from anaplastic astrocytoma, astrocytoma, central neurocytoma, choroid plexus carcinoma, choroid plexus papilloma, choroid plexus tumour, diffuse intrinsic pontine glioma, dysembryoplastic neuroepithelial tumour, ependymal tumour, fibrillary astrocytoma, giant-cell glioblastoma, glioblastoma multiforme, gliomatosis cerebri, gliosarcoma, hemangiopericytoma, medulloblastoma, medulloepithelioma, meningeal carcinomatosis, neuroblastoma, neurocytoma, oligoastrocytoma, oligodendroglioma, optic nerve sheath meningioma, paediatric ependymoma, pilocytic astrocytoma, pinealoblastoma, pineocytoma, pleomorphic anaplastic neuroblastoma, pleomorphic xanthoastrocytoma, primary central nervous system lymphoma, sphenoid wing meningioma, subependymal giant cell astrocytoma, subependymoma and trilateral retinoblastoma. Therefore, preferably, the brain cancer is a tumour (preferably, a solid tumour). The brain cancer may be a primary cancer (e.g. a glioma, a meningioma, a pituitary adenoma or a nerve sheath tumour) or a metastatic cancer (i.e. a brain cancer that has arisen as a result of cancer in other parts of the body, such as melanoma or lung cancer).

Alternatively, or in addition to, the compounds may be administered in combination with other agents, for example, chemotherapeutic or immune-stimulating drugs or therapeutic agents.

The terms "combination therapy" or "adjunct therapy" in defining use of a compound of the present invention and one or more other pharmaceutical agents, are intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations of each agent.

In accordance with various embodiments of the present invention one or more compounds of formula (I) may be formulated or administered in combination with one or more other therapeutic agents. Therefore, in accordance with various embodiments of the present invention, one or more compounds of formula (I) may be included in combination treatment regimens with surgery and/or other known treatments or therapeutic agents, such as other anticancer agents, in particular, chemotherapeutic agents, radiotherapeutic agents, and/or adjuvant or prophylactic agents.

There are large numbers of antineoplastic agents available in commercial use, in clinical evaluation and in pre-clinical development, which could be selected for treatment of cancers or other neoplasias by combination drug chemotherapy. Such anti-neoplastic agents fall into several major categories, namely, antibiotic-type agents, antimetabolite agents, hormonal agents, immunological agents, interferon-type agents and a category of miscellaneous agents. Alternatively, other anti-neoplastic agents, such as metallomatrix proteases inhibitors may be used. Suitable agents which may be used in combination therapy will be recognized by those of skill in the art. Suitable agents are listed, for example, in the Merck Index, An Encyclopaedia of Chemicals, Drugs and Biologicals, 12th Ed., 1996.

Combination regimens may involve the active agents being administered together, sequentially, or spaced apart as appropriate in each case. Combinations of active agents including compounds of the invention may be synergistic.

The co-administration of compounds of formula (I) may be effected by a compound of formula (I) being in the same unit dose as a chemotherapeutic or other anti-cancer agent, or the compound of formula (I) and the chemotherapeutic or other anti-cancer agents may be present in individual and discrete unit doses administered at the same, or at a similar time. Sequential administration may be in any order as required, and may require an ongoing physiological effect of the first or initial compound to be current when the second or later compound is administered, especially where a cumulative or synergistic effect is desired.

For various applications, the compounds of the invention can be labelled by isotopes, fluorescence or luminescence markers, antibodies or antibody fragments, any other affinity label like nanobodies, aptamers, peptides etc., enzymes or enzyme substrates. These labelled compounds of this invention are useful for mapping the location of receptors in vivo, ex vivo, in vitro and in situ such as in tissue sections via autoradiography and as radiotracers for positron emission tomography (PET) imaging, single photon emission computerized tomography (SPECT) and the like, to characterize those receptors in living subjects or other materials. The labelled compounds according to the present invention may be used in therapy, diagnosis and other applications such as research tools in vivo and in vitro, in particular the applications disclosed herein.

It will be understood that the invention disclosed and defined in this specification extends to all alternative combinations of two or more of the individual features mentioned or evident from the text or drawings. All of these different combinations constitute various alternative aspects of the invention.

Embodiments of the invention will now be discussed in more detail with reference to the examples which is provided for exemplification only and which should not be considered limiting on the scope of the invention in any way.

EXAMPLES

All chemicals were obtained from Sigma-Aldrich (St. Louis, Mo., USA), except for boronic acids that were purchased from Frontiers Scientific (Logan, Utah, USA). Microwave irradiation was carried out using the CEM-Discover microwave reactor (Kamp-Lintfort, Germany). $^1$H-NMR spectra were obtained on a BRUKER "Avance 300" 300 MHz NMR spectrometer (Bruker Corp., Billerica, Mass., USA). $d_6$-DMSO or $CDCl_3$ were obtained from Cambridge Isotope Laboratories. High performance liquid chromatography was conducted on an Agilent series 1200 LC system with an Agilent 1260 Infinity binary pump and integrated vacuum degasser, autosampler and diode array detector (Agilent Technologies, Santa Clara, Calif., USA). The samples were analyzed on an Agilent C18 column (particle size: 5 µM, 150×4.6 mm internal diameter) using an acetonitrile:water gradient of 0 to 100% over 40 min and at a flow rate of 0.2 mL/min. A sample of elution was analysed using the Agilent 6120 quadrupole mass spectrometer. Agilent OpenLAB Chromatography Data System (CDS) ChemStation Edition was used for data acquisition and processing.

Primary antibodies against Bcl-2, PARP (#95425), secondary anti-rabbit (#7074) and anti-mouse (#7076) HRP-linked antibodies were obtained from Cell Signaling Technology (Danvers, Mass., USA). EGFR (# sc03) and GAPDH (# sc737179) antibodies were from Santa Cruz Biotechnology (Dallas, Tex., USA). Antibody against β-tubulin (# ab11308) was purchased from Abcam. Alexa488-conjugated anti-mouse secondary antibody and DAPI (4',6'-diamino-2-phenylindole) were from Life Technologies. CMPD1 (# sc-203138) was obtained from Santa Cruz Biotechnology. Paclitaxel and vinblastine were purchased from Sigma.

Synthesis
See also Scheme 1 for preparation of compounds.

4-(4-bromophenyl)-4-oxobutanoic acid 4

Succinic anhydride 3 (5.0 g, 50 mmol) and bromobenzene 2 (48 g, 300 mmol) were cooled to 0° C. Aluminium chloride (13.3 g, 100 mmol) was added and the mixture was stirred for 4 h at 0° C. under nitrogen atmosphere. The reaction was allowed to warm to room temperature and stirred for 96 h under nitrogen atmosphere. The reaction was cooled to 0° C. and concentrated HCl (125 mL) was added and reaction stirred under nitrogen for a further 1 h. The reaction was filtered and washed with water (1 L) to obtain a pale yellow solid which was recrystallised from toluene to yield 4-(4-bromophenyl)-4-oxobutanoic acid 4 (12 g, 46.68 mmol, 93.4%).

MS (ESI-QUADRUPOLE) m/z: calc. for $C_{10}H_9BrO_3$: 255.97, 257.97; Found: 258.0 (11), 257.0 (98), 256.0 (12), 255.0 (100), 213.0 (18), 211.0 (17) (negative ions).

HPLC: $t_r$=24.4 min $^1$H NMR (500 MHz, $d_6$-DMSO) δ: 2.59 (2H, t, J=6.5 Hz, $CH_2$), 3.21 (2H, t, J=6.5 Hz, $CH_2$), 7.88 (2H, d, J=8.8 Hz, ArH), 7.96 (2H, d, J=8.8 Hz, ArH), 12.19 (1H, br s, OH).

4-(4-bromophenyl)butanoic acid 5

Zinc (13.0 g, 200 mmol) and mercury chloride (1.00 g, 480 mmol) were stirred with water (10 mL) and concentrated HCl (0.6 mL) for five minutes. The liquid was decanted off and toluene (20 mL), concentrated HCl (20 mL) and water (8 mL) were added consecutively. 4-(4-bromophenyl)-4-oxobutanoic acid 4 (2.55 g, 10.5 mmol) was added and heated under reflux at 100° C. for 24 h adding HCl (1 mL) every 6 h. The reaction was allowed to cool to room temperature, filtered and the solvent removed from the organic layer to give a clear liquid which gave white crystals upon cooling. These were purified with silica gel chromatography (ethyl acetate:hexane, 1:3) to yield 4-(4-bromophenyl)butanoic acid 5 (2.33 g, 9.63 mmol, 91.4%).

MS (ESI-QUADRUPOLE) m/z: calc. for $C_{10}H_{11}BrO_2$: 241.99, 243.99; Found: 244.0 (10), 243.0 (98), 242.0 (11), 241.0 (100) (negative ions).

HPLC: $t_r$=27.7 min.

$^1$H NMR (300 MHz, $CDCl_3$) (δ/ppm) 7.40 (2H, d, J=8.4 Hz, ArH), 7.06 (2H, d, J=8.4 Hz, ArH), 2.63 (2H, t, J=7.8 Hz, $CH_2$), 2.36 (2H, t, J=7.2 Hz, $CH_2$), 1.97, (2H, dt, J=7.2, 7.8 Hz, $CH_2$), OH not observed.

4-(4-bromophenyl)-N-(4-hydroxyphenyl)butanamide 7 (1-17)

4-(4-bromophenyl)butanoic acid 4 (0.5 g, 2.07 mmol) and benzotriazol-1-yl-oxytripyrrolidinophosphonium hexafluorophosphate (PyBOP (1.07 g, 2.07 mmol) were dissolved in dimethylformamide (10 mL). Diisopropylethylamine (710 µL, 4.14 mmol) was added and the reaction stirred at 00° C. for 30 minutes. 4-aminophenol 6 (0.269 mg, 2.48 mmol) was added and the reaction stirred at room temperature for 12 h. The reaction was diluted with water (90 mL) and the product extracted with dichloromethane (3×50 mL). The solvent was removed and the product purified by silica gel chromatography (ethyl acetate:hexane, gradient 35:65 to 60:40) to yield 4-(4-bromophenyl)-N-(4-hydroxyphenyl)butanamide 7 as a white solid (350 mg, 1.05 mmol, 51%).

MS (ESI-QUADRUPOLE) m/z: calc. for $C_{16}H_{16}BrNO_2$: 333.04, 335.04; Found: 334.0 (100), 335.0 (18), 336.0 (93), 337.0 (17).

HPLC: $t_r$=28.2 min.

$^1$H NMR (300 MHz, $d_6$-DMSO) (δ/ppm) 9.59 (1H, br s, NH), 9.15 (1H, br s, OH), 7.47 (2H, d, J=8.1 Hz, ArH), 7.33 (2H, d, J=9.0 Hz, ArH), 7.18 (2H, d, J=8.4 Hz, ArH), 6.67 (2H, d, J=8.7 Hz, ArH), 2.59 (2H, t, J=7.8 Hz, $CH_2$), 2.24 (2H, t, J=7.2 Hz, $CH_2$), 1.85 (2H, dt, J=7.2, 7.8 Hz, $CH_2$).

4-(4-(2-fluoropyridin-3-yl)phenyl)-N-(4-hydroxyphenyl)butanamide 10 (1-18)

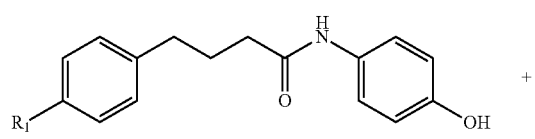

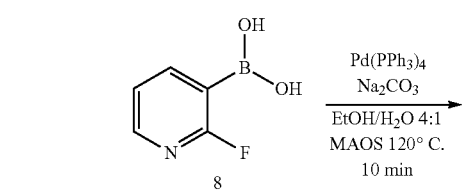

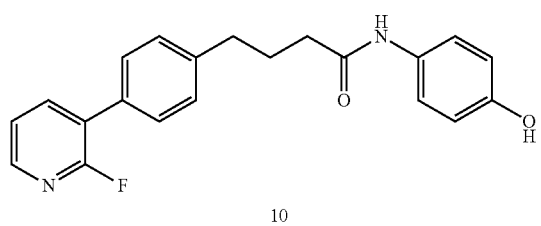

4-(4-bromophenyl)-N-(4-hydroxyphenyl)butanamide 7 (100 mg, 0.3 mmol), (2-fluoropyridin-3-yl)boronic acid 8 (50.9 mg, 0.361 mmol), sodium carbonate (63.8 mg, 0.6 mmol) and tetrakis(triphenylphosphine)palladium(0) (17 mg, 0.015 mmol) were dissolved in ethanol:water (4:1 v/v, 2 mL). The solution was purged with nitrogen and heated in a sealed tube with microwave irradiation (power moderated 50 W starting, pressure uncontrolled) at 120° C. for 10 min. The reaction was cooled and the solvent removed to give a yellow solid. The product was purified by silica gel chromatography (ethyl acetate:hexane, gradient 45:100 to 60:40) to yield 4-(4-(2-fluoropyridin-3-yl)phenyl)-N-(4-hydroxyphenyl)butanamide 10 as an off white solid (40 mg, 0.11 mmol, 38%).

MS (ESI-QUADRUPOLE) m/z: calc for $C_{21}H_{19}FN_2O_2$: 350.14; Found: 351.2 (100), 352.2 (24).

HPLC: $t_r$=26.1 min.

$^1$H NMR (300 MHz, $d_6$-DMSO) (δ/ppm) 9.61 (1H, br s, NH), 9.12 (1H, br s, OH), 8.23 (1H, d, J=2.4 Hz, ArH), 8.09 (1H, tt, J=8.4 Hz, 2.4, ArH), 7.54 (2H, d, J=8.4 Hz, ArH), 7.47 (4H, d, J=8.7 Hz, ArH), 7.44 (1H, d, J=4.2 Hz, ArH), 6.68 (2H, d, J=8.7 Hz, ArH), 2.68 (2H, t, J=7.8 Hz, $CH_2$), 2.30 (2H, t, J=7.5 Hz, $CH_2$), 1.93 (2H, dt, J=7.8, 7.5 Hz, $CH_2$).

4-(4-(2,6-difluoropyridin-3-yl)phenyl)-N-(4-hydroxyphenyl)butanamide 12 (1-22)

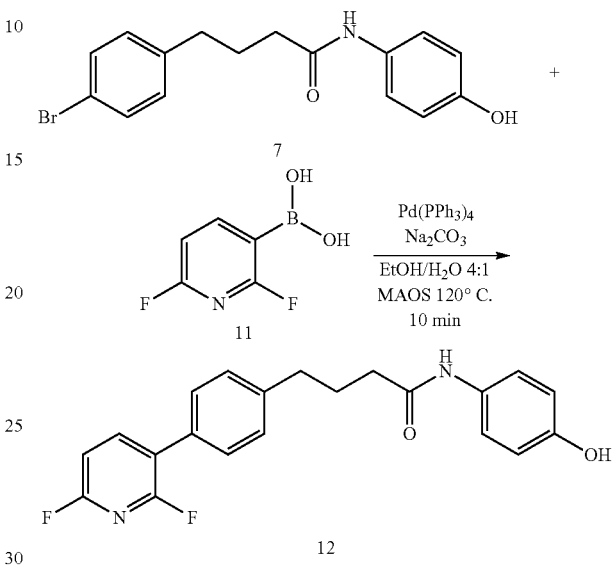

4-(4-bromophenyl)-N-(4-hydroxyphenyl)butanamide 7 (100 mg, 0.3 mmol), (2,6-difluoropyridin-3-yl)boronic acid 11 (57.0 mg, 0.36 mmol), sodium carbonate (63.8 mg, 0.6 mmol) and tetrakis(triphenylphosphine)palladium(0) (17 mg, 0.015 mmol) were dissolved in ethanol:water (4:1 v/v, 2 mL). The solution was purged with nitrogen and heated in a sealed tube with microwave irradiation (power moderated 50 W starting, pressure uncontrolled) at 120° C. for 10 min. The reaction was cooled and the solvent removed to give a yellow solid. The product was purified by silica gel chromatography (ethyl acetate:hexane, gradient 25:100 to 50:50) to yield 4-(4-(2,6-difluoropyridin-3-yl)phenyl)-N-(4-hydroxyphenyl)butanamide 12 as an off white solid (30 mg, 0.08 mmol, 27%).

MS (ESI-QUADRUPOLE) m/z: calc for $C_{21}H_{18}F_2N_2O_2$: 368.13; Found: 369.1 (100), 370.1 (23).

HPLC: $t_r$=28.6 min.

$^1$H NMR (300 MHz, $d_6$-DMSO) (δ/ppm) 9.62 (1H, br s, NH), 9.17 (1H, br s, OH), 8.29 (1H, dt, J=7.5, 5.0 Hz, ArH), 7.52 (2H, d, J=6.6 Hz, ArH), 7.35 (4H, m, ArH), 7.27 (1H, dd, J=8.4, 2.7 Hz, ArH), 6.67 (2H, d, J=9 Hz, ArH), 2.67 (2H, t, J=7.8 Hz, $CH_2$), 2.29 (2H, t, J=7.5 Hz, $CH_2$), 1.91 (2H, dt, J=7.8, 7.5 Hz, $CH_2$).

4-(4-(6-fluoropyridin-3-yl)phenyl)-N-(4-hydroxyphenyl)butanamide 14 (1-21)

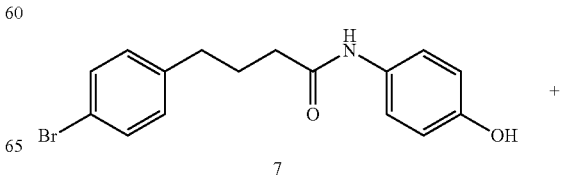

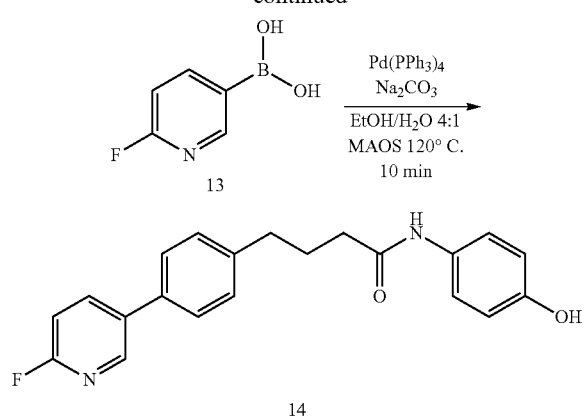

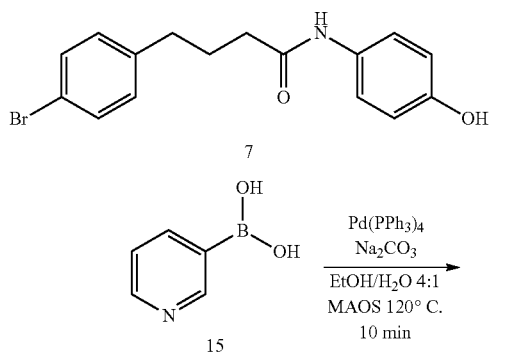

4-(4-bromophenyl)-N-(4-hydroxyphenyl)butanamide 7 (100 mg, 0.299 mmol), (6-fluoropyridin-3-yl)boronic acid 13 (50.96 mg, 0.359 mmol), sodium carbonate (63.8 mg, 0.600 mmol) and tetrakis(triphenylphosphine)palladium(0) (17 mg, 0.015 mmol) were dissolved in ethanol:water (4:1 v/v, 2 mL). The solution was purged with nitrogen and heated in a sealed tube with microwave irradiation (power moderated 50 W starting, pressure uncontrolled) at 120° C. for 10 min. The reaction was cooled and the solvent removed to give a yellow solid. The product was purified by silica gel chromatography (ethyl acetate:hexane, gradient 25:100 to 50:50) to yield 4-(4-(6-fluoropyridin-3-yl)phenyl)-N-(4-hydroxyphenyl)butanamide 14 as an off white solid (30 mg, 0.09 mmol, 29%).

MS (ESI-QUADRUPOLE) m/z: calc. for $C_{21}H_{19}FN_2O_2$: 350.14; Found: 351.1 (100), 352.1 (23).

HPLC: $t_r$=26.8 min.

$^1$H NMR (300 MHz, $d_6$-DMSO) (δ/ppm) 9.61 (1H, br s, NH), 9.16 (1H, br s, OH), 8.52 (1H, d, J=2.4 Hz, ArH), 8.25 (1H, tt, J=8.4 Hz, 2.4, ArH), 7.64 (2H, d, J=8.4 Hz, ArH), 7.34 (4H, d, J=8.7 Hz, ArH), 7.26 (1H, dd, J=4.2, 3.0 Hz, ArH), 6.66 (2H, d, J=8.7 Hz, ArH), 2.66 (2H, t, J=7.8 Hz, $CH_2$), 2.28 (2H, t, J=7.5 Hz, $CH_2$), 1.90 (2H, dt, J=7.8, 7.5 Hz, $CH_2$).

N-(4-hydroxyphenyl)-4-(4-(pyridin-3-yl)phenyl)butanamide 16 (1-38)

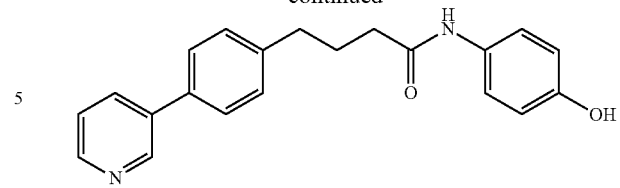

4-(4-bromophenyl)-N-(4-hydroxyphenyl)butanamide 7 (100 mg, 0.3 mmol), pyridin-3-ylboronic acid 15 (67.1 mg, 0.36 mmol), sodium carbonate (63.8 mg, 0.6 mmol) and tetrakis(triphenylphosphine)palladium(0) (17 mg, 0.015 mmol) were dissolved in ethanol:water (4:1 v/v, 2 mL). The solution was purged with nitrogen and heated in a sealed tube with microwave irradiation (power moderated 50 W starting, pressure uncontrolled) at 120° C. for 10 min. The reaction was cooled and the solvent removed to give a yellow solid. The product was purified by silica gel chromatography (ethyl acetate:hexane, gradient 25:100 to 50:50) to yield N-(4-hydroxyphenyl)-4-(4-(pyridin-3-yl)phenyl)butanamide 16 as an off white solid (40 mg, 0.11 mmol, 35%).

MS (ESI-QUADRUPOLE) m/z: calc. for $C_{21}H_{20}N_2O_2$: 332.15; Found: 333.2 (100), 334.1 (23).

HPLC: $t_r$=17.3 min.

$^1$H NMR (300 MHz, $d_6$-DMSO) (δ/ppm) 9.62 (1H, br s, NH), 9.16 (1H, br s, OH), 8.88 (1H, s, ArH), 8.55 (1H, d, J=4.5 Hz, ArH), 8.05 (1H, d, J=7.8 Hz, ArH), 7.66 (2H, d, J=7.8 Hz, ArH), 7.48 (1H, q, J=4.8 Hz, ArH), 7.35 (4H, d, J=8.4 Hz, ArH), 6.67 (2H, d, J=8.7), 2.68 (2H, t, J=6.9 Hz, $CH_2$), 2.29 (2H, t, J=7.5 Hz, $CH_2$), 1.92 (2H, dt, J=6.9, 7.5 Hz, $CH_2$).

N-(4-hydroxyphenyl)-4-(4-(2-methoxypyrimidin-5-yl)phenyl)butanamide 18 (1-19)

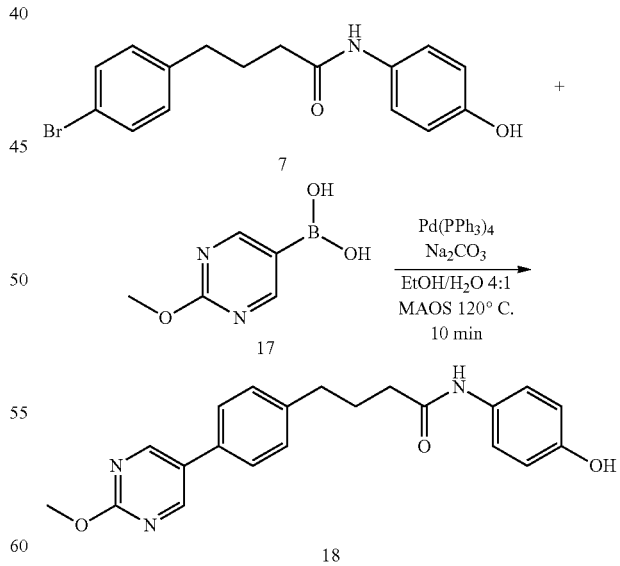

4-(4-bromophenyl)-N-(4-hydroxyphenyl)butanamide 7 (100 mg, 0.299 mmol), (2-methoxypyrimidin-5-yl)boronic acid 17 (55.25 mg, 0.359 mmol), sodium carbonate (63.8 mg, 0.600 mmol) and tetrakis(triphenylphosphine)palladium(0) (17 mg, 0.015 mmol) were dissolved in ethanol:

water (4:1 v/v, 2 mL). The solution was purged with nitrogen and heated in a sealed tube with microwave irradiation (power moderated 50 W starting, pressure uncontrolled) at 120° C. for 10 min. The reaction was determined by thin layer chromatography to have low conversion and was therefore heated with microwave irradiation as before for a further 20 min. The solvent was removed and the product purified by silica gel chromatography (ethyl acetate:hexane, gradient 25:100 to 50:50) to yield 4-(4-(6-fluoropyridin-3-yl)phenyl)-N-(4-hydroxyphenyl)butanamide 18 as an off white solid (3 mg, 0.08 mmol, 3%).

MS (ESI-QUADRUPOLE) m/z: calc. for $C_{21}H_{21}N_3O_3$: 363.16; Found: 364.2 (100), 365.2 (24).

HPLC: $t_r$=24.3 min.

4-(4-bromophenyl)-N-phenylbutanamide 20

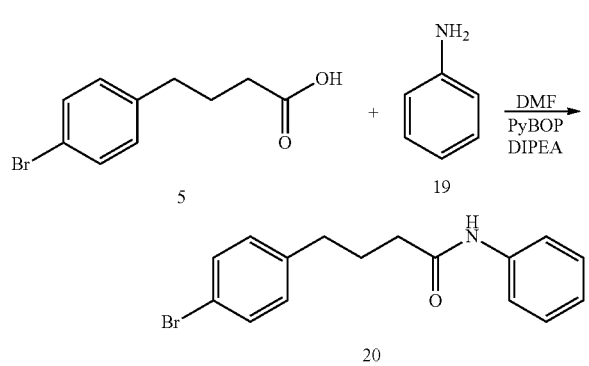

4-(4-bromophenyl)butanoic acid 5 (0.5 g, 2 mmol) and benzotriazol-1-yl-oxytripyrrolidinophosphonium hexafluorophosphate (PyBOP) (1.07 g, 2.07 mmol) were dissolved in dimethyl formamide (10 mL). Diisopropylethylamine (710 µL, 4.14 mmol) was added and the reaction stirred at 00° C. for 30 minutes. Aniline 19 (225.0 µL, 2.47 mmol) was added and the reaction stirred at room temperature for 12 h. The reaction was then diluted with water (90 mL) and the product extracted with dichloromethane (3×50 mL). The solvent was removed and the product purified by silica gel chromatography (ethyl acetate:hexane, gradient 20:80 to 40:60) to yield 4-(4-bromophenyl)-N-phenylbutanamide 20 as a white solid (500 mg, 1.57 mmol, 76%).

MS (ESI-QUADRUPOLE) m/z: calc. for $C_{16}H_{16}BrNO$: 317.04, 319.04; Found: 318.1 (100), 319.1 (19), 320.1 (96), 321.1 (17), 340.0 (33), 341.0 (6), 342.0 (33), 343.0 (5).

HPLC: $t_r$=35.7 min.

$^1$H NMR (300 MHz, $d_6$-DMSO) (δ/ppm) 9.85 (1H, br s, NH), 7.57 (2H, d, J=7.5 Hz, ArH), 7.46 (2H, d, J=8.4 Hz, ArH), 7.27 (2H, t, J=8.1 Hz, ArH), 7.18 (2H, d, J=8.4 Hz, ArH), 7.01 (1H, t, J=7.2 Hz, ArH), 2.60 (2H, t, J=7.2 Hz, $CH_2$), 2.30, (2H, t, J=7.5 Hz, $CH_2$), 1.87 (2H, dt, J=7.2, 7.5 Hz, $CH_2$).

4-(4-(2-fluoropyridin-3-yl)phenyl)-N-phenylbutanamide 21 (1-20)

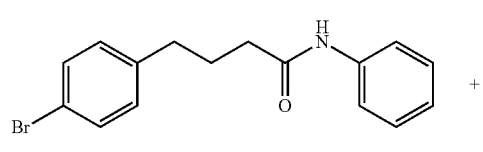

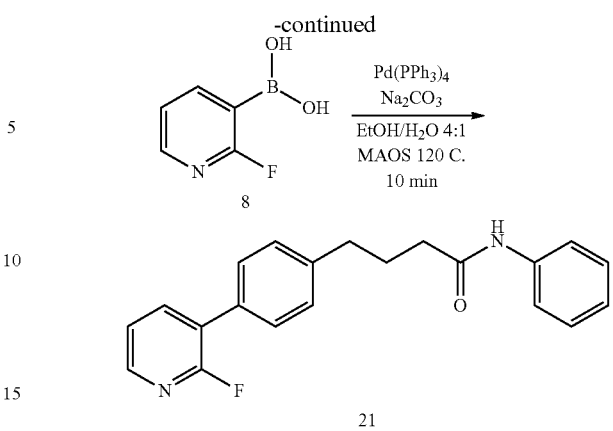

4-(4-bromophenyl)-N-phenylbutanamide 20 (100 mg, 0.314 mmol), (2-fluoropyridin-3-yl)boronic acid 8 (52.8 mg, 0.377 mmol), sodium carbonate (66.7 mg, 0.628 mmol) and tetrakis(triphenylphosphine)palladium(0) (17 mg, 0.015 mmol) were dissolved in ethanol:water (4:1 v/v, 2 mL). The solution was purged with nitrogen and heated in a sealed tube with microwave irradiation (power moderated 50 W starting, pressure uncontrolled) at 120° C. for 10 min. The reaction was cooled and the solvent removed to give a yellow solid. The product was purified by silica gel chromatography (ethyl acetate:hexane, gradient 30:100 to 60:40) to yield 4-(4-(2-fluoropyridin-3-yl)phenyl)-N-phenylbutanamide 21 as a yellow solid (30 mg, 0.11 mmol, 38%).

MS (ESI-QUADRUPOLE) m/z: $C_{21}H_{19}FN_2O$: 334.15; Found 335.2 (100), 336.2 (23), 357.2 (14).

HPLC: $t_r$=31.1 min.

$^1$H NMR (300 MHz, $d_6$-DMSO) (δ/ppm) 9.85 (1H, br s, NH), 8.22 (1H, d, J=4.8 Hz, ArH), 8.09 (1H, ddd, J=10.2, 4.8, 1.8 Hz, ArH), 7.56 (4H, m, ArH), 7.36 (2H, d, J=8.4 Hz, ArH), 7.28 (2H, t, J=8.4 Hz, ArH), 7.01 (1H, t, J=7.2 Hz, ArH), 2.68 (2H, t, J=7.5 Hz, $CH_2$), 2.35, (2H, t, J=7.5 Hz, $CH_2$), 1.94 (2H, q, J=7.5, 7.5 Hz, $CH_2$).

N-(4-hydroxyphenyl)-4-(4-(pyrimidin-5-yl)phenyl) butanamide (1-01)

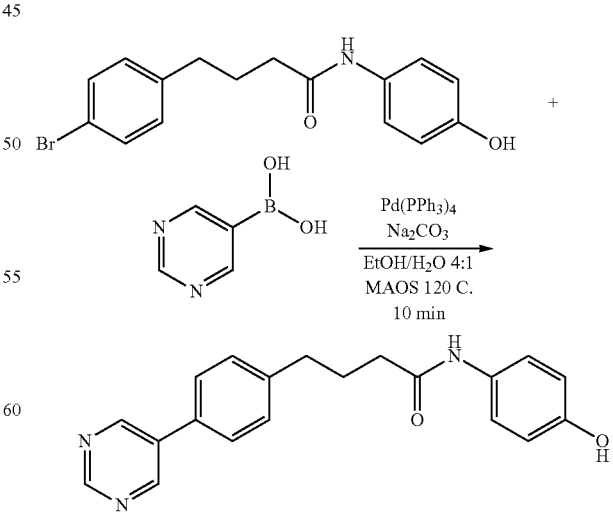

4-(4-bromophenyl)-N-(4-hydroxyphenyl)butanamide (100 mg, 0.3 mmol), pyrimidin-5-ylboronic acid (44.8 mg, 0.361 mmol), sodium carbonate (64 mg, 0.6 mmol) and tetrakis(triphenylphosphine)palladium(0) (21 mg, 0.018 mmol) were dissolved in ethanol:water (4:1 v/v, 2 mL). The solution was purged with nitrogen and heated in a sealed tube with microwave irradiation (power moderated 50 W starting, pressure uncontrolled) at 120° C. for 10 min. The reaction was cooled and the solvent removed to give a yellow solid. The product was purified by silica gel chromatography (ethyl acetate:hexane, gradient 35:75 to 85:15) to yield N-(4-hydroxyphenyl)-4-(4-(pyrimidin-5-yl)phenyl) butanamide as an off white solid (20 mg, 0.06 mmol, 20%).

$^1$H NMR (300 MHz, d$_6$-DMSO) (δ/ppm) 9.61 (1H, br s, NH), 9.16 (1H, br s, OH), 9.13 (3H, m, ArH), 7.74 (2H, d, J=8.1 Hz, ArH), 7.38 (4H, m, ArH), 6.66 (2H, d, J=8.7 Hz, ArH), 2.68 (2H, t, J=7.2 Hz, CH$_2$), 2.29 (2H, t, J=7.2 Hz, CH$_2$), 1.92 (2H, m, CH$_2$).

4-(4'-(aminomethyl)-[1,1'-biphenyl]-4-yl)-N-(4-hydroxyphenyl)butanamide (1-07)

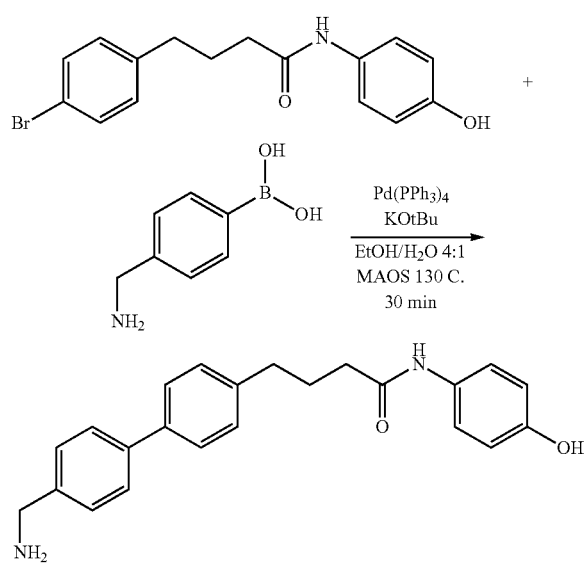

4-(4-bromophenyl)-N-(4-hydroxyphenyl)butanamide (101 mg, 0.3 mmol), (4-(aminomethyl)phenyl)boronic acid (71 mg, 0.38 mmol), potassium tert-butoxide (75 mg, 0.45 mmol) and tetrakis(triphenylphosphine)palladium(0) (27 mg, 0.02 mmol) were dissolved in ethanol:water (4:1 v/v, 2 mL). The solution was purged with nitrogen and heated in a sealed tube with microwave irradiation (power moderated 50 W starting, pressure uncontrolled) at 130° C. for 30 min. The reaction was cooled and the solvent removed to give a yellow solid. The product was purified by silica gel chromatography (methanol:dichloromethane, gradient 5:95 to 15:85) to yield 4-(4'-(aminomethyl)-[1,1'-biphenyl]-4-yl)-N-(4-hydroxyphenyl)butanamide as an off white solid (30 mg, 0.08 mmol, 30%).

$^1$H NMR (300 MHz, d$_6$-DMSO) (δ/ppm) 9.62 (1H, br s, OH), 7.57 (4H, m, ArH), 7.34 (6H, m, ArH), 6.67 (2H, d, J=8.7 Hz, ArH), 3.75 (2H, s, CH$_2$), 2.64 (2H, t, J=7.5 Hz, CH$_2$), 2.28 (2H, t, J=7.5 Hz, CH$_2$), 1.896 (2H, m, CH$_2$).

N-(4-hydroxyphenyl)-4-(4-(quinolin-3-yl)phenyl) butanamide (1-08)

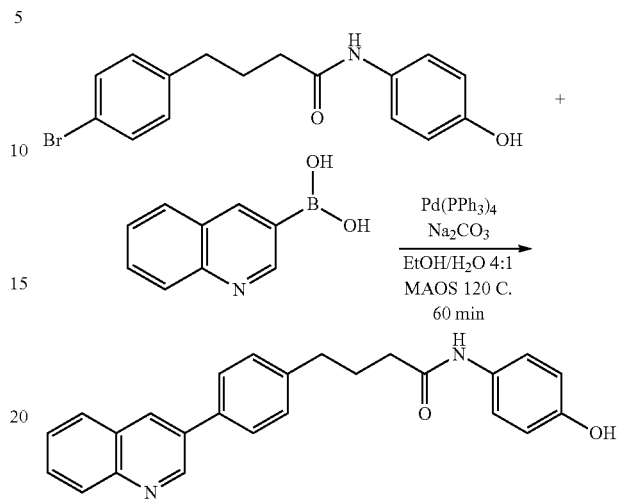

4-(4-bromophenyl)-N-(4-hydroxyphenyl)butanamide (105 mg, 0.31 mmol), quinolin-3-ylboronic acid (65 mg, 0.38 mmol), sodium carbonate (55 mg, 0.52 mmol) and tetrakis(triphenylphosphine)palladium(0) (21 mg, 0.018 mmol) were dissolved in ethanol:water (4:1 v/v, 2 mL). The solution was purged with nitrogen and heated in a sealed tube with microwave irradiation (power moderated 50 W starting, pressure uncontrolled) at 120° C. for 60 min. The reaction was cooled and the solvent removed to give a yellow solid. The product was purified by flash silica gel chromatography (ethyl acetate:hexane, gradient 0:100 to 100:0 over 60 min) to yield N-(4-hydroxyphenyl)-4-(4-(quinolin-3-yl)phenyl)butanamide as an off white solid (30 mg, 0.08 mmol, 25%).

$^1$H NMR (400 MHz, d$_6$-DMSO) (δ/ppm) 9.61 (1H, br s, NH), 9.25 (1H, s, ArH), 9.11 (1H, br s, OH), 8.62 (1H, s, ArH), 8.05 (2H, d, J=8.4 Hz, ArH), 7.82 (2H, d, J=8.4 Hz, ArH), 7.77 (1H, t, J=8.0 Hz, ArH), 7.61 (1H, m, ArH), 7.38 (4H, m, ArH), 6.67 (2H, d, J=8.8 Hz, ArH), 2.70 (2H, t, J=7.6 Hz, CH$_2$), 2.31 (2H, t, J=7.6 Hz, CH$_2$), 1.95 (2H, m, CH$_2$).

Biological Evaluation

U87 and U251 cell lines were obtained from the European Collection of Cell Cultures (ECACC) through CellBank Australia. U87-EGFRvIII cell line was obtained from their lab of origin (Nishikawa et al., 1994, *Proc Natl Acad Sci USA* 91: 7727-7731) and tested for EGFR amplification and mutation by immunoblotting and flow cytometry. Cells were cultured in DMEM medium (Invitrogen by Life Technologies, Carlsbad, Calif., USA) supplemented with 10% FBS (Sigma-Aldrich) at 37° C. and 5% CO$_2$. Primary gliomaspheres (RN1, classical; WK1, mesenchymal) were derived from glioblastoma specimens (Day et al., 2013, *Cancers* 5: 357-371; Day et al., 2013, *Cancer Cell* 23: 238-248), maintained in StemPro NSC serum-free media supplemented with EGF and FGF (all Life Technologies), and grown on matrigel-coated flasks (Pollard et al., 2009, *Cell Stem Cell* 4: 568-580).

EC$_{50}$ Values of Compounds of the Present Invention.

Cell viability was determined using Alamar blue assay after 72 hours of treatment (Table 2). EC$_{50}$ values were calculated using non-linear regression on Graph Pad Prism version 5. c Log P values calculated using ChemBioDraw Software. Results are mean±SEM from three independent experiments performed in triplicates.

Further Analysis

Figure 1B:
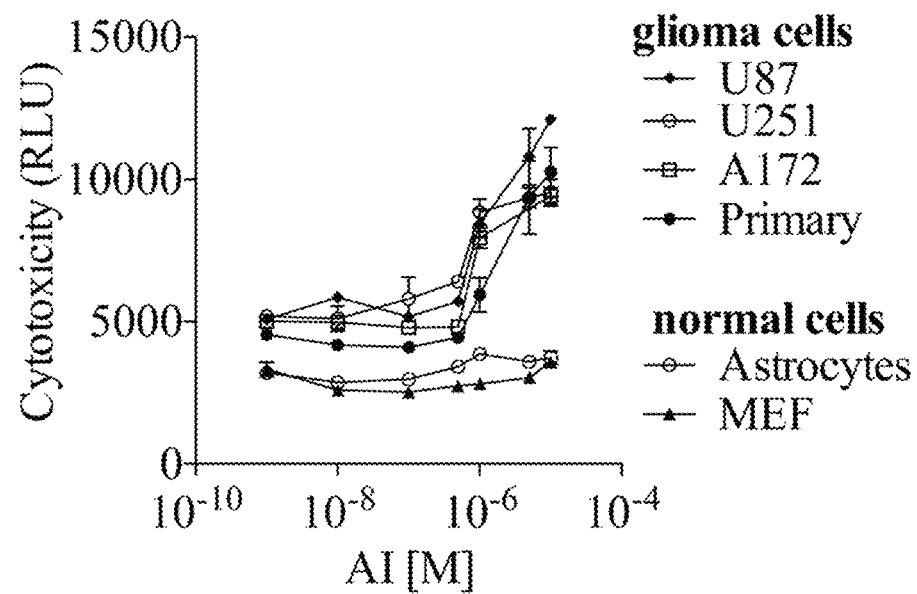

As shown in FIG. 1, SC-38 decreases viability of glioma cell lines and is selectively cytotoxic. Cells were treated with

TABLE 2

EC$_{50}$ values of compounds of the present invention

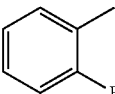

| Compound | R$_1$ | R$_2$ | c LogP | EC$_{50}$ ± SEM (μM) U87 | U87vIII | U251 |
|---|---|---|---|---|---|---|
| SC-38 | 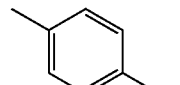 | 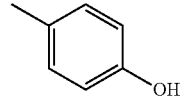 | 5.0 | 0.38 ± 0.1 | 0.68 ± 0.1 | 0.43 ± 0.1 |
| SB-1-17 | Br— | 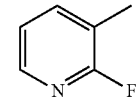 | 3.8 | >10 | >10 | >10 |
| SB-1-20 | 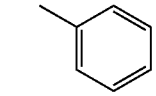 | 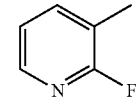 | 4.3 | 6.6 ± 0.9 | >10 | 4.6 ± 0.2 |
| SB-1-18 | 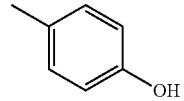 | 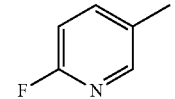 | 3.6 | 1.4 ± 0.2 | 1.7 ± 0.1 | 1.6 ± 0.2 |
| SB-1-21 | 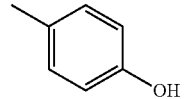 | 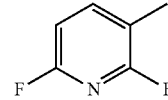 | 4.3 | 4.8 ± 1.2 | >10 | >10 |
| SB-1-22 | 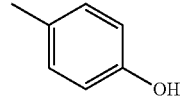 | 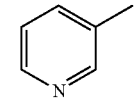 | 3.7 | 2.9 ± 0.9 | 3.4 ± 0.4 | 1.65 ± 0.1 |
| SB-1-38 | 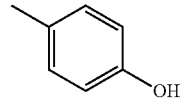 | 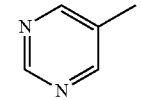 | 3.4 | 4.6 ± 0.8 | 4.3 ± 0.3 | 1.2 ± 0.1 |
| AD-1-01 | 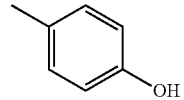 | 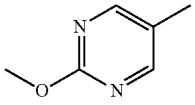 | 2.4 | >10 | >10 | >10 |
| SB-1-19 | 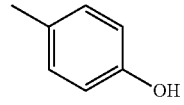 | 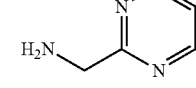 | 3.3 | >10 | >10 | >10 |
| AD-1-07 | 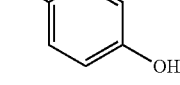 | 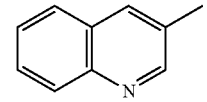 | 3.8 | 1.8 ± 0.3 | 3.1 ± 1.0 | 1.5 ± 0.3 |
| AD-1-08 | 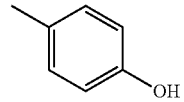 | | 4.7 | 0.65 ± 0.3 | 1.3 ± 0.4 | 0.98 ± 0.2 |

SC-38 (10 nM-10 μM) for 72 hours. Cells were subjected to viability testing (left, Alamar Blue viability assay, Invitrogen) and supernatant harvested for bioluminescent cytotoxicity analysis (right, ToxiLight™ bioassay kit, Lonza).

Figure 2:
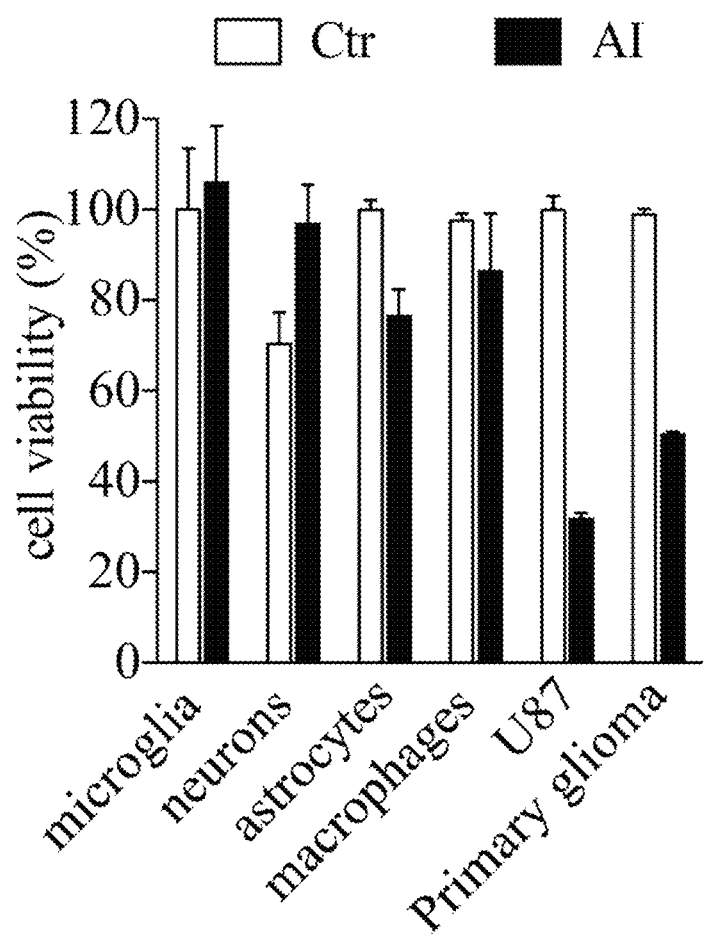
FIG. 2. Results of treatment of various cancer cell lines with SC-38 to test cytotoxicity of SC-38 in respect of malignant cells.

As shown in FIG. 2, SC-38 is selectively toxic to malignant cells. Cells were treated with SC-38 (1 μM) for 72 hours and viability assays (AlamarBlue, MTT or PI staining) was performed to determine viability of malignant (U87, primary glioma) and non-malignant (microglia, neurons, astrocytes, macrophages) cells.

Figure 3:
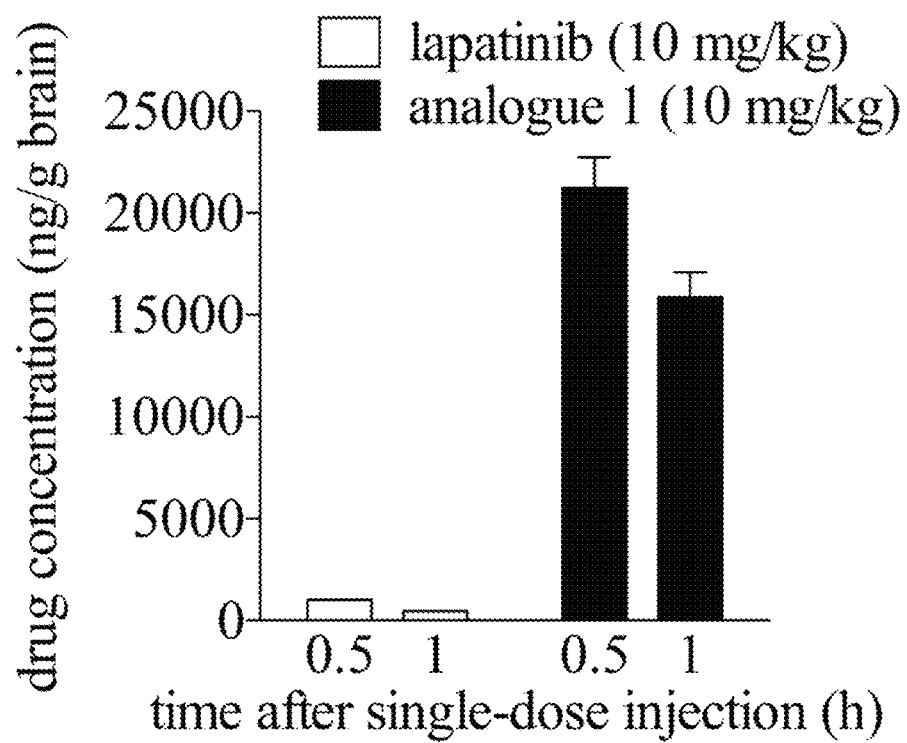
FIG. 3. Brain uptake of compound 1-18.
Figure 4A:
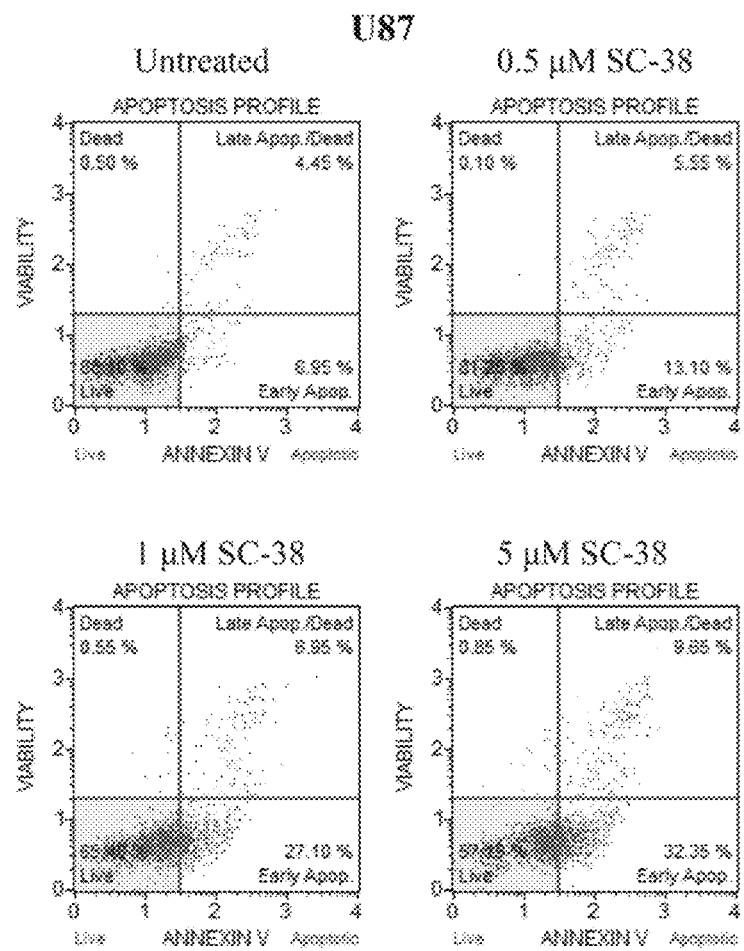
FIGS. 4A-4D. SC-38-induced apoptosis in U87 and U87vIII cells. U87 (4A-4B) and U87vIII (4C-4D) cells were treated with SC-38 for 48 hours and stained with Annexin-FITC/7-AAD. Apoptotic cells were visualized using the MUSE cell analyzer (Millipore).
Figure 4B:
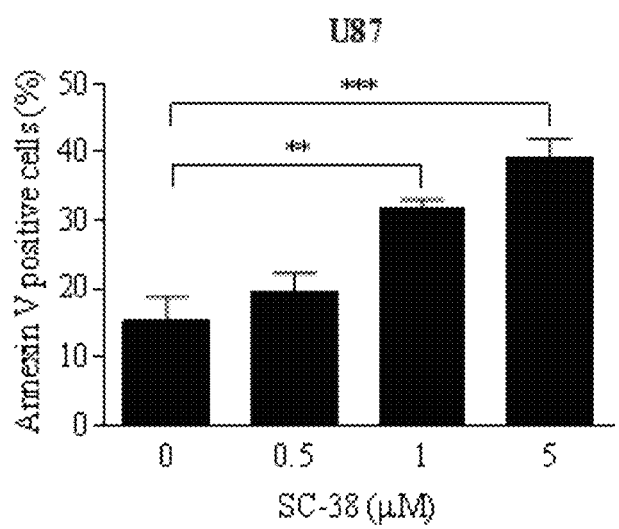
Figure 4C:
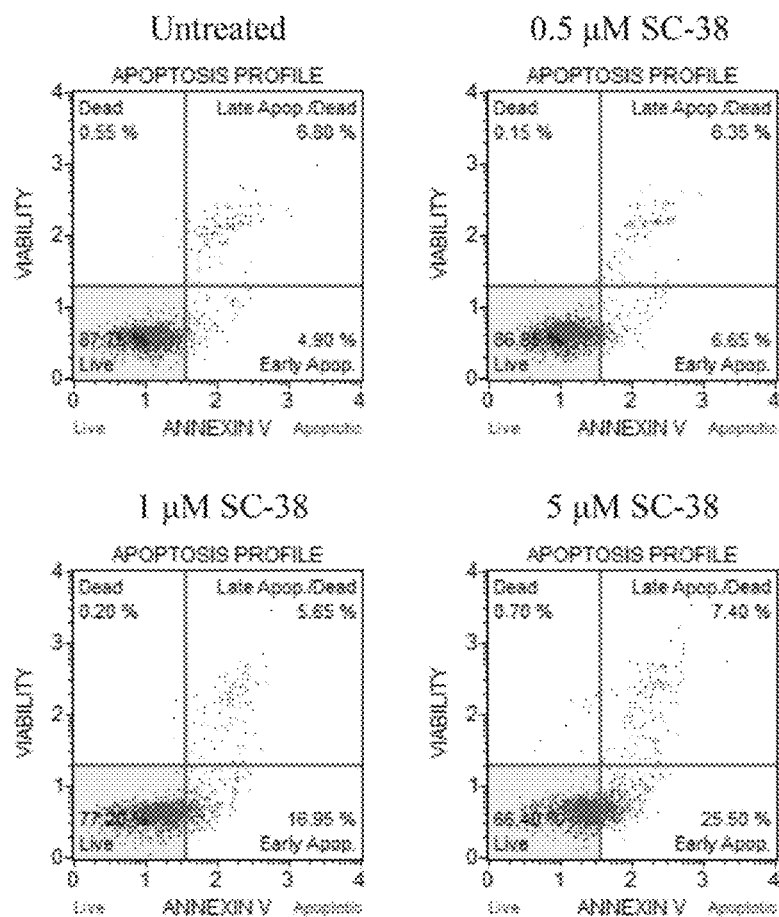
Figure 4D:
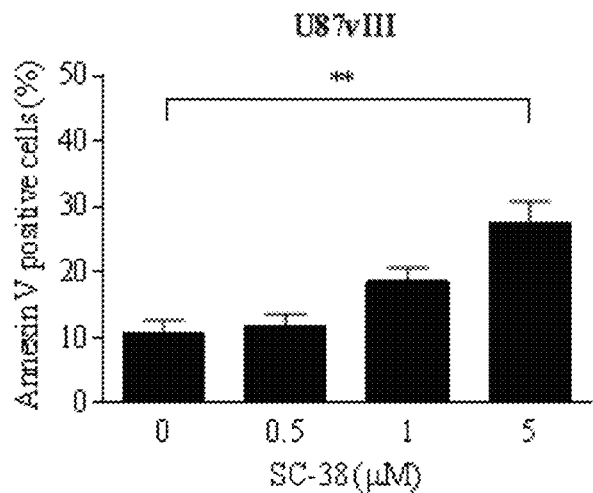

As shown in FIG. 3, compound 1-18 readily crossed the BBB. BALB/c mice were injected intraperitoneally with tested inhibitor (10 mg/kg) and brains harvested at 30 and 60 min. Solid-phase extraction was performed using brain homogenates and the amount of the test compound was determined with HPLC. Lapatinib data are from Polli, J. W. et al. "The Role of Efflux and Uptake Transporters in N-{3-Chloro-4-[(3-fluorobenzyl)oxy]phenyl}-6-[5-({[2-(methylsulfonyl)ethyl]amino}methyl)-2-furyl]-4-quinazolinamine (GW572016, Lapatinib) Disposition and Drug Interactions", Drug Metabolism and Disposition 36, 695-701 (2008).

As shown in FIG. 4, SC-38 induced apoptosis in U87 and U87vIII cells. U87 (FIGS. 4, A-B) and U87vIII (FIG. 4, C-D) cells were treated with SC-38 for 48 hours and stained with Annexin-FITC/7-AAD. Apoptotic cells were visualized using the MUSE cell analyzer (Millipore). Results are means±SEM from 3 independent experiments. One-way ANOVA followed by Dunnet post-test was used to calculate statistical significance (P<0.01, *P<0.001)

Figure 5A:
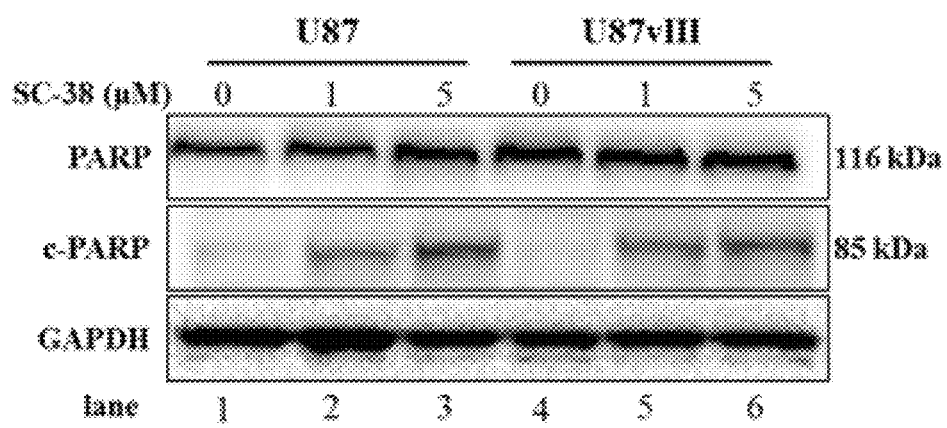
FIGS. 5A-5B. Western Blot analysis of PARP cleavage in U87 and U87vIII cells after SC-38 treatment. (5A) U87 (lanes 1-3) and U87vIII (lanes 4-6) cells were treated with 1 and 5 µM of SC-38 for 48 hours. A representative blot of 3 independent experiments is shown. GAPDH was used as a loading control. (5B) PARP cleavage was quantified and normalized against GAPDH (expressed as fold change). Results are mean±SEM from 3 independent experiments. Statistical significance was determined using One-way ANOVA followed by Dunnet post-test (* $P<0.05$, * $P<0.001$, ** $P<0.0001$).
Figure 5B:
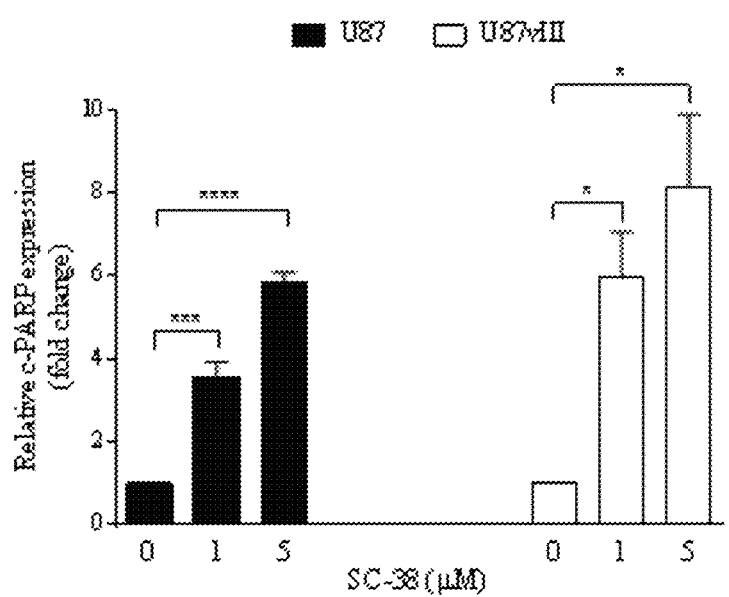
Figure 6A:
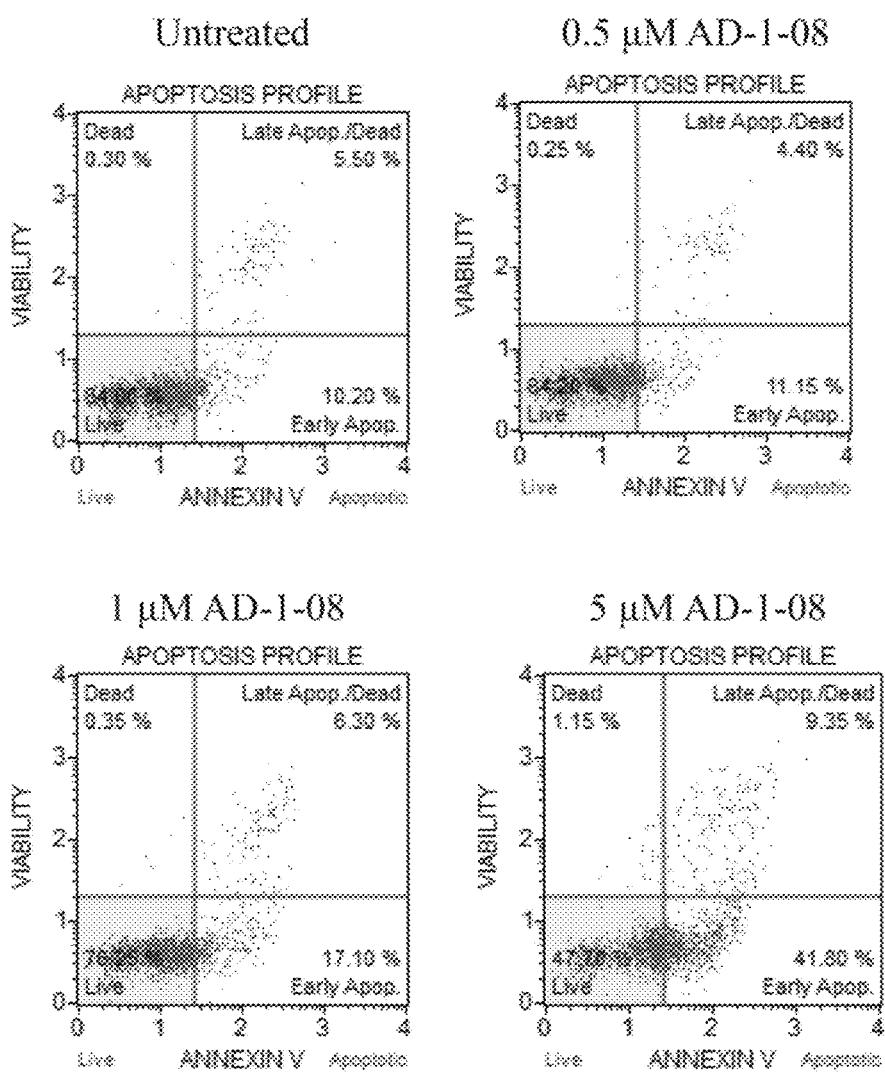
FIGS. 6A-6D. Compound 1-08 induced apoptosis in U87 and U87vIII cells. U87 (A B) (6A-6B) and U87vIII (6C-6D) cells were treated with compound 1-08 for 48 hours and stained with Annexin-FITC/7-AAD. Apoptotic cells were visualized using the MUSE cell analyzer (Millipore). Results are means±SEM from 3 independent experiments. One-way ANOVA followed by Dunnet post-test was used to calculate statistical significance (*** $P<0.001$).
Figure 6B:
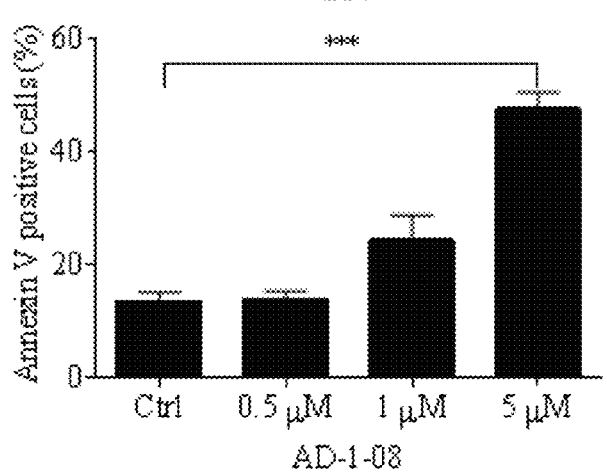
Figure 6C:
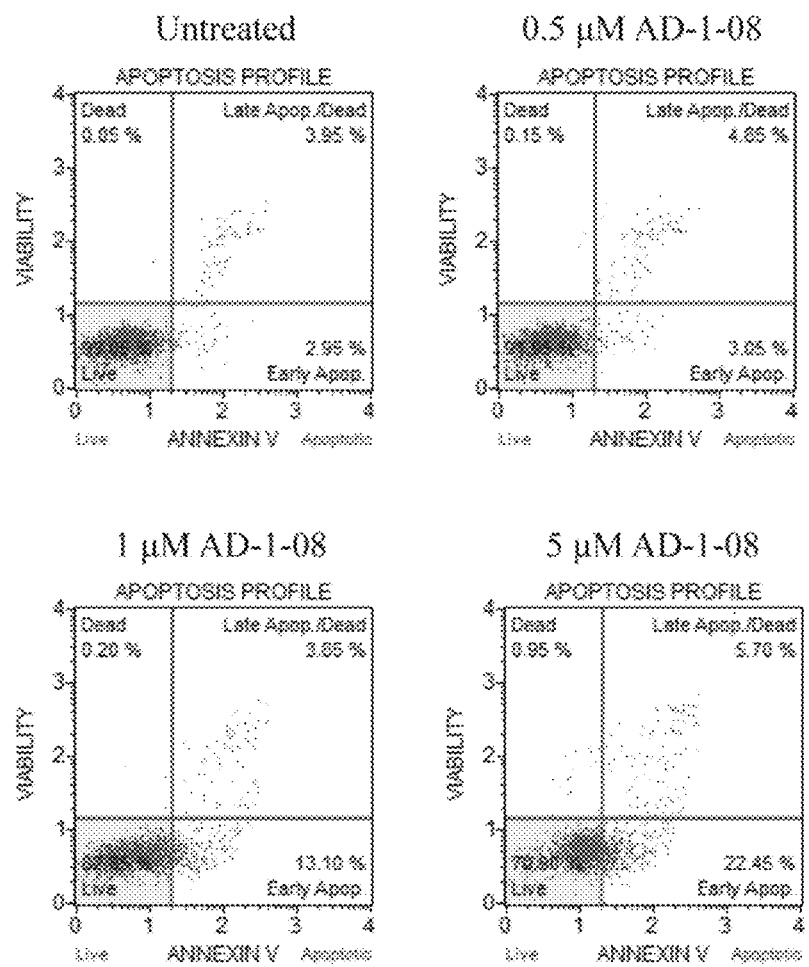
Figure 6D:
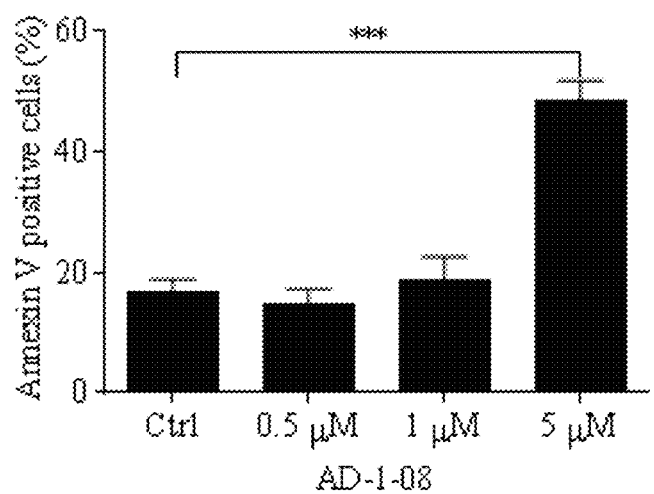

Western Blot analysis of PARP cleavage in U87 and U87vIII cells after SC-38 treatment was also conducted (see FIG. 5). U87 (lanes 1-3) and U87vIII (lanes 4-6) cells were treated with 1 and 5 μM of SC-38 for 48 hours. A representative blot of 3 independent experiments is shown (FIG. 5 A). GAPDH was used as a loading control. PARP cleavage was quantified and normalized against GAPDH (expressed as fold change), see FIG. 5 B. Results are mean±SEM from 3 independent experiments. Statistical significance was determined using One-way ANOVA followed by Dunnet post-test (* P<0.05, * P<0.001, ** P<0.0001).

As shown in FIG. 6, compound 1-08 induced apoptosis in U87 and U87vIII cells. U87 (FIGS. 6, A-B) and U87vIII (FIG. 6, C-D) cells were treated with compound 1-08 for 48 hours and stained with Annexin-FITC/7-AAD. Apoptotic cells were visualized using the MUSE cell analyzer (Millipore). Results are means±SEM from three independent experiments. One-way ANOVA followed by Dunnet post-test was used to calculate statistical significance (***P<0.001).

Figure 7A:
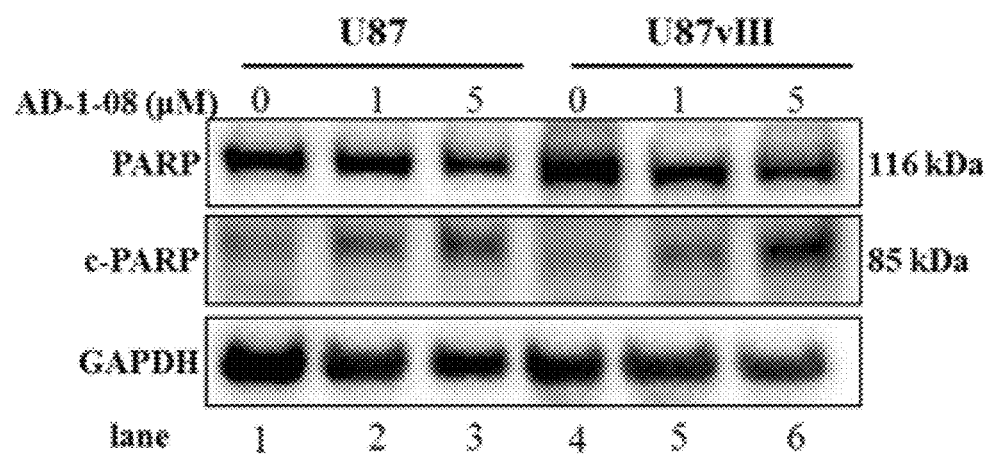
FIGS. 7A-7B. Western Blot analysis of PARP cleavage in U87 and U87vIII cells after compound 1-08 treatment. (7A) U87 (lanes 1-3) and U87vIII (lanes 4-6) cells were treated with 1 and 5 µM of compound 1-08 for 48 hours. A representative blot of 3 independent experiments is shown. GAPDH was used as a loading control. (7B) Cleavage of PARP was quantified and normalized against GAPDH (expressed as fold change). Results are mean±SEM from 3 independent experiments. Statistical significance was determined using One-way ANOVA followed by Dunnet post-test (* $P<0.05$, **** $P<0.0001$).
Figure 7B:
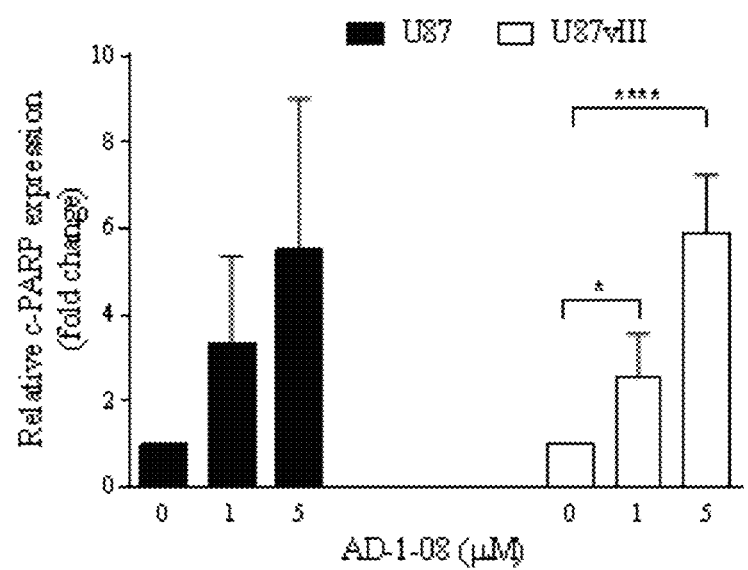
Figure 8A:
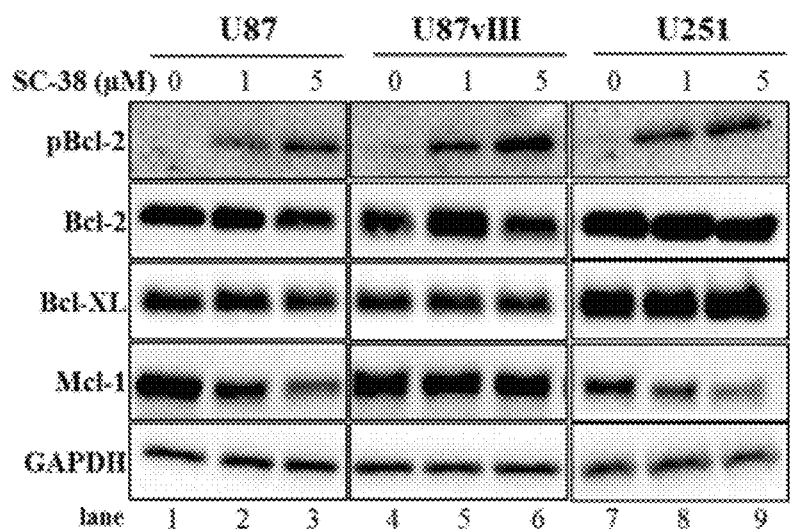
FIGS. 8A-8E. The effect of SC-38 treatment on Bcl-2 family proteins in U87, U87vIII and U251. U87 (lanes 1-3), U87vIII (lanes 4-6) and U251 (lanes 7-9) cells were treated with SC-38 (1 and 5 µM) for 24 hours and subjected to Western blot analysis where GAPDH was used as a loading control. Representative blot is shown in (8A) and quantifications normalized to GAPDH are shown in (8B-8E) presented as fold-change. Results are mean±SEM from three independent experiments, and unpaired t-test was used to determine statistical significance (* $P<0.05$,  $P<0.01$, ** $P<0.0001$).
Figure 8B:
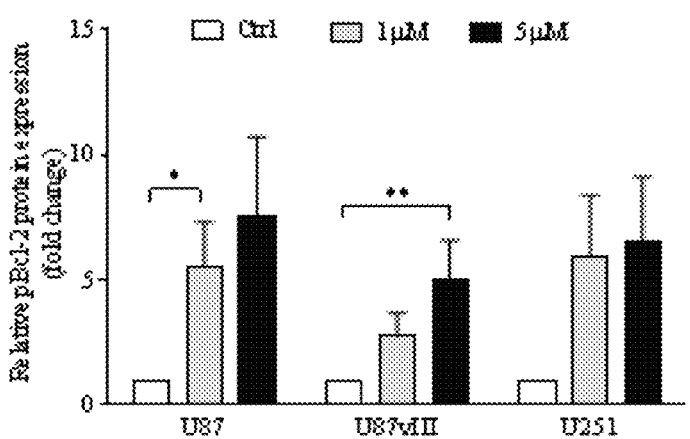
Figure 8C:
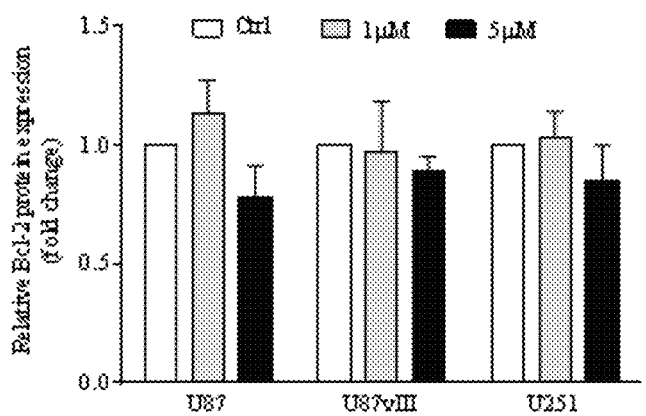
Figure 8D:
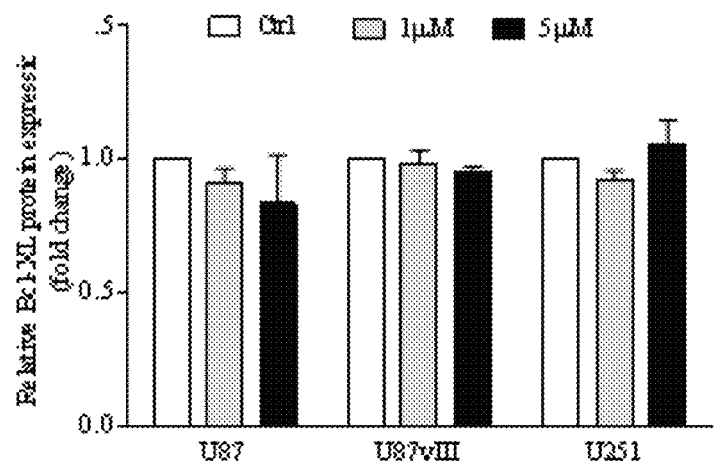
Figure 8E:
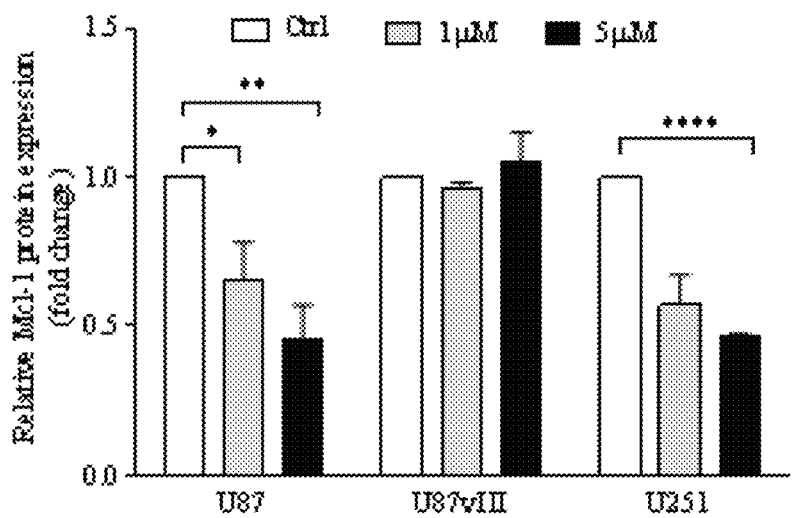
Figure 9A:
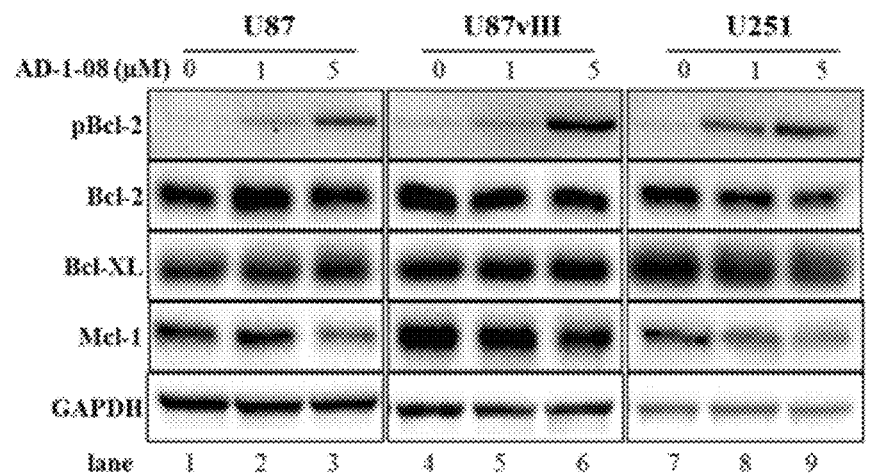
FIGS. 9A-9E. The effect of compound 1-08 treatment on Bcl-2 family proteins in U87, U87vIII and U251. U87 (lanes 1-3), U87vIII (lanes 4-6) and U251 (lanes 7-9) cells. Representative blot is shown in (9A) and quantifications shown in (9B-9E) presented as relative protein expression. Results are mean±SEM from 2 independent experiments, and unpaired t-test was used to determine statistical significance (* $P<0.05$, ** $P<0.01$).
Figure 9B:
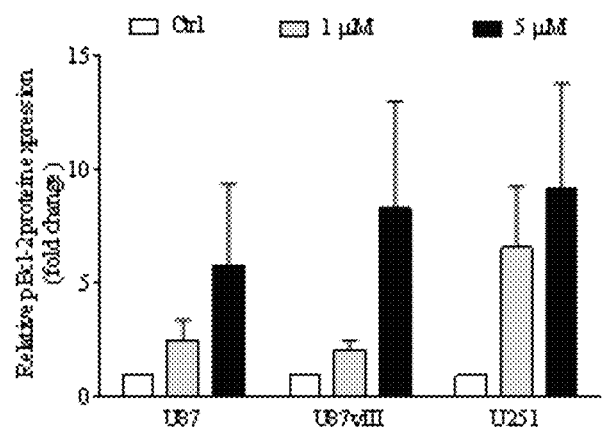
Figure 9C:
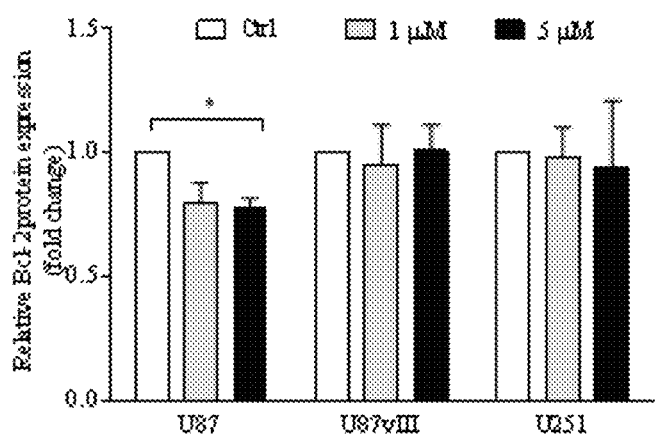
Figure 9D:
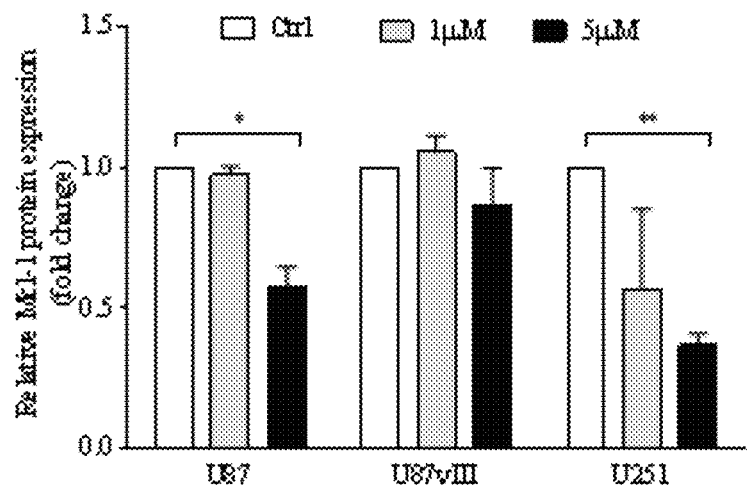
Figure 9E:
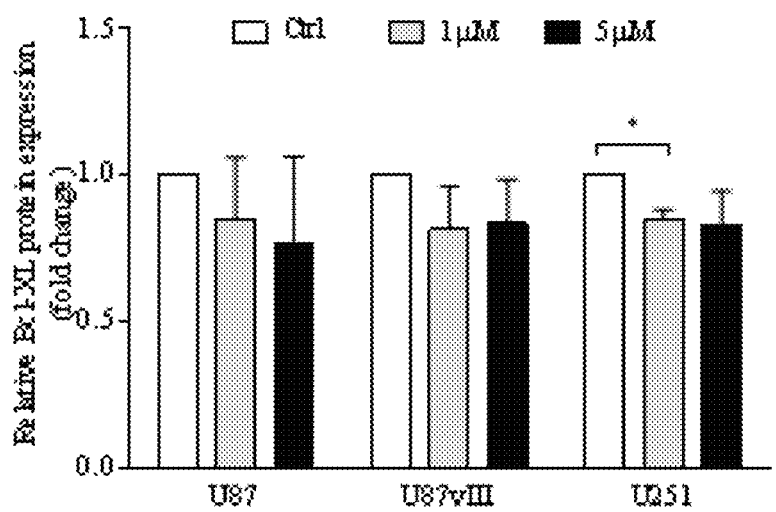

Western Blot analysis of PARP cleavage in U87 and U87vIII cells after compound 1-08 treatment was also conducted (FIG. 7). U87 (lanes 1-3) and U87vIII (lanes 4-6) cells were treated with 1 and 5 μM of compound 1-08 for 48 hours. A representative blot of 3 independent experiments is shown (see FIG. 7 A). GAPDH was used as a loading control. Cleavage of PARP was quantified and normalized against GAPDH (expressed as fold change), see FIG. 7 B. Results are mean±SEM from 3 independent experiments. Statistical significance was determined using One-way ANOVA followed by Dunnet post-test (* P<0.05, **** P<0.0001).

The effect of SC-38 treatment on Bcl-2 family proteins in U87, U87vIII and U251 was also tested (see FIG. 8). U87 (lanes 1-3), U87vIII (lanes 4-6) and U251 (lanes 7-9) cells were treated with SC-38 (1 and 5 μM) for 24 hours and subjected to Western blot analysis where GAPDH was used as a loading control. Representative blot is shown in FIG. 8 A and quantifications normalized to GAPDH are shown in FIG. 8 B-E presented as fold-change. Results are mean±SEM from three independent experiments, and unpaired t-test was used to determine statistical significance (* P<0.05,  P<0.01, ** P<0.0001).

The effect of compound 1-08 treatment on Bcl-2 family proteins in U87, U87vIII and U251 was also investigated (see FIG. 9). U87 (lanes 1-3), U87vIII (lanes 4-6) and U251 (lanes 7-9) cells were treated with compound 1-08 (1 and 5 μM) for 24 hours and subjected to Western blot analysis where GAPDH was used as a loading control. Representative blot is shown in FIG. 9 A and quantifications are shown in FIG. 9 B-E presented as relative protein expression. Results are mean±SEM from 2 independent experiments, and unpaired t-test was used to determine statistical significance (* P<0.05, ** P<0.01).

The kinase profiling of compound 1-08 at 10 and 50 μM was performed by ProQinase GmbH (Freiburg, Germany). A radiometric protein kinase assay ($^{33}$PanQinase® Activity Assay) and the non-radiometric ADP-Glo™ Assay (Promega, Madison, Wis., USA) were used for measuring kinase activity of 387 protein kinases and 13 lipid kinases, respectively. The results are shown in Table 3 (only the top 10 kinases are listed, and the selectivity score describes the portion of kinases inhibited more than 50% in relation to all tested kinases).

TABLE 3

Kinome profile of compound 1-08

| Kinase | residual activity (%) in the presence of cmpd 13 | |
|---|---|---|
| | 10 μM | 50 μM |
| ALK | 76 | 21 |
| BRK | 74 | 29 |
| CSK | 89 | 21 |
| EPHB1 | 57 | 20 |
| IGF1R | 73 | 15 |
| LYN | 87 | 21 |
| MERK | 49 | 12 |
| RON | 84 | 18 |
| SRC | 57 | 21 |
| ZAP90 | 60 | 14 |
| Selectivity score | 0.003 | 0.203 |

At 10 μM, compound 1-08 inhibited MERTK at the 51% level. Several other kinases were inhibited at 50 μM concentration.

Figure 10A:
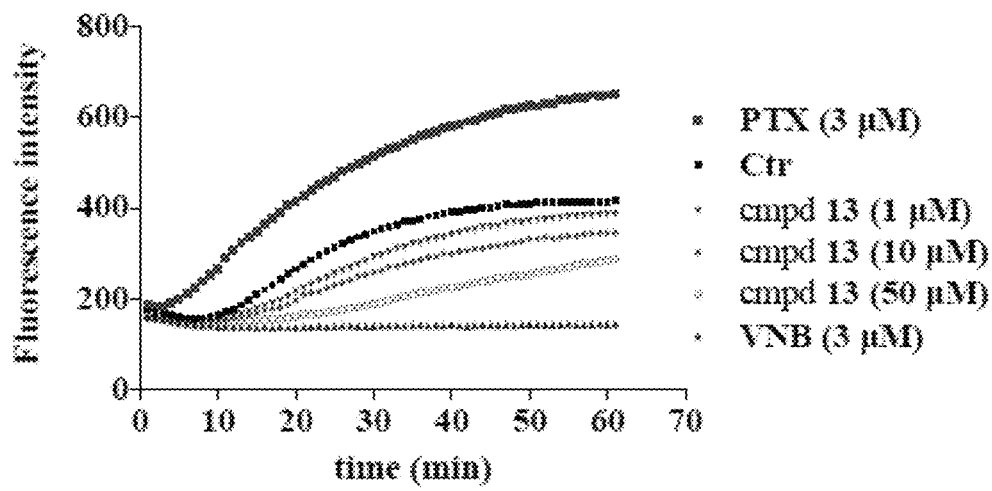
FIGS. 10A-10D. Compound 1-08 (referred to as "cmpd 13" and "compound 13") exhibits a mechanism of action consistent with microtubule disruption. (10A) Compound 1-08 inhibits tubulin polymerisation in vitro. Data are expressed as mean from at least 3 independent experiments; each data point was performed in triplicates. (10B) U87 cells treated with compound 1-08 (24 h) were stained with Alexa488-labelled anti-β-tubulin antibody (green) or DAPI (blue). Treatment profoundly disturbed the microtubule network and caused formation of multinucleated cell (white arrows). White scale bar represents 50 µm. Multinucleated cells were manually counted and at least 200 cells were counted for each sample. Data in the bar graph (10C) are expressed as mean±SEM (n=3; * $P<0.05$, *** $P<0.001$; 1-way ANOVA followed by Newman-Keuls posttest). (10D) U87 cells were treated with compound 1-08 (48 h), tubulin and DNA were stained as in (10B). Treatment with 1-08 caused defective mitotic spindle formation. Representative images from 3 independent experiments are shown. White scale bar represents 2 µm.
Figure 10B:
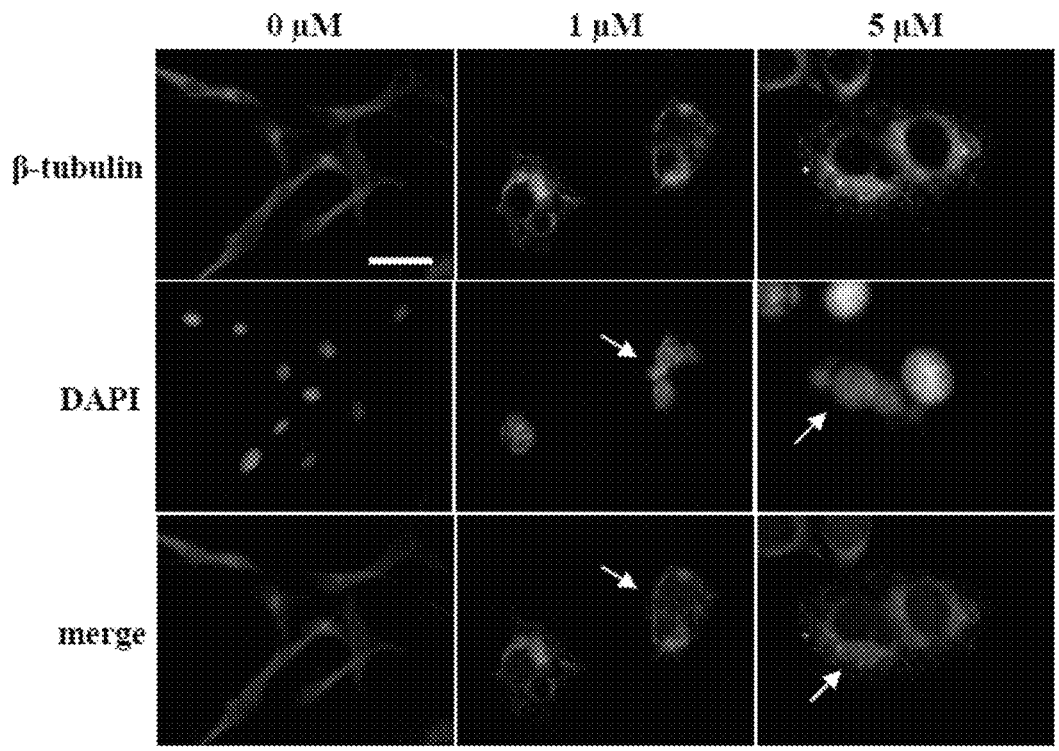
Figure 10C:
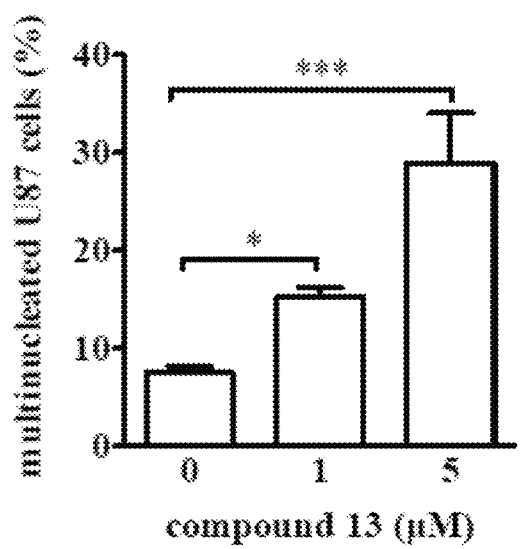
Figure 10D:
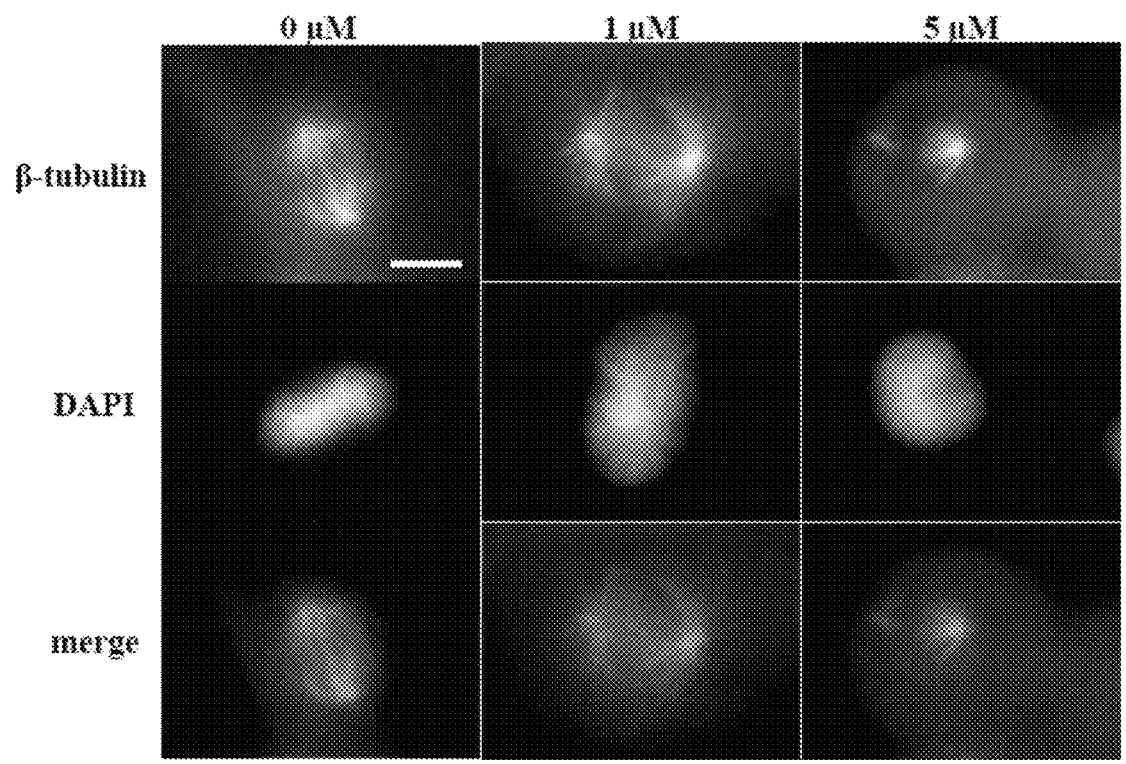

The effect of compound 1-08 on tubulin polymerisation and mitotic spindle formation was also investigated. The fluorescence-based tubulin polymerisation assay was conducted in the final volume of 55 μL using the Tubulin Polymerisation Assay kit (Cytoskeleton, Colo., USA) as per the manufacturer's instructions. Porcine brain tubulin was incubated with test compounds (paclitaxel, vinblastine and compound 1-08) at 37° C. and fluorescence was measured using FLUOstar Omega microplate reader (BMG Labtech, Ortenberg, Germany; excitation at 355 nm and emission at 460 nm). Compared to control, paclitaxel enhanced tubulin polymerisation, whereas vinblastine and compound 1-08 inhibited tubulin polymerisation in a dose-dependent manner (FIG. 10A). To test whether compound 1-08 alters microtubules in vivo, U87 glioblastoma cells were treated with compound 1-08 and the effect on the microtubules was determined by immunofluorescence staining of β-tubulin. Treatment of U87 cells with compound 1-08 (1 and 5 μM)

led to a disassembly of microtubules (FIG. 10B) and dose-dependent increase in the number of multinucleated cells (FIGS. 10B and 10C). The consequence of microtubule depolymerisation induced by compound 13 was disrupted spindle assembly (FIG. 10D). In untreated U87 cells undergoing mitosis, microtubules are assembled into bipolar spindles (control images). However, treatment with compound 1-08 resulted in defective spindle formation and chromosome misalignment. These results indicate that compound 1-08 is a tubulin-depolymerising agent that disrupts the mitotic spindle formation and causes formation of multinucleated cells.

Figure 11A:
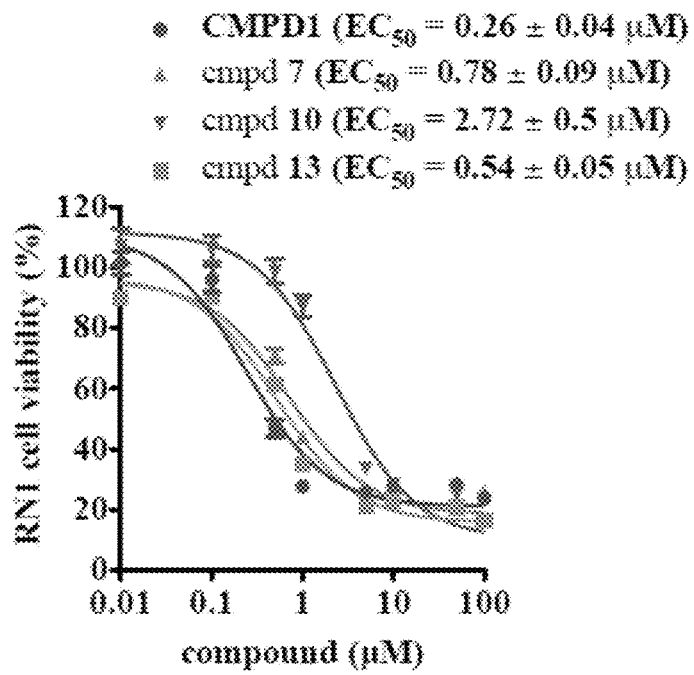
FIGS. 11A-11B. Efficacy of SC-38 (referred to as "CMPD1"), compound 1-08 (referred to as "cmpd 13"), compound 1-18 (referred to as "cmpd 7"), and compound 1-38 (referred to as "cmpd 10") in primary gliomaspheres representing two glioblastoma subtypes. (11A) RN1, classical, and (11B) WK1, mesenchymal. Cellular efficacy ($EC_{50}$) of test compounds was determined using AlamarBlue cell viability assay after 72 h of drug treatment. Data are mean±SEM from 3 independent experiments performed in triplicate.
Figure 11B:
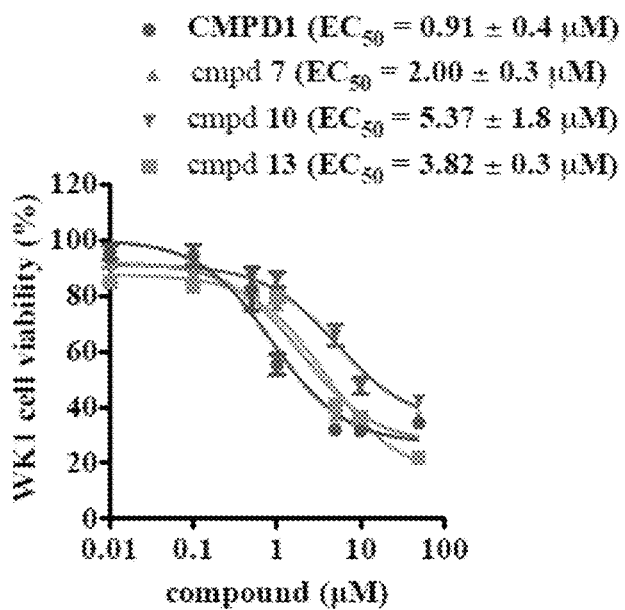

The effect of SC-38, and compounds 1-08, 1-18 and 1-38 in a cell viability assay employing patient-derived gliomaspheres was also investigated. RN1 gliomaspheres representing glioblastoma of the classical subtype were most responsive to the treatment (FIG. 11, where SC-38 is referred to as "CMPD1", compound 1-08 is referred to as "compound 13", compound 1-18 is referred to as "compound 7", and compound 1-38 is referred to as "compound 10"). SC-38 and compound 1-08 attenuated viability of RN1 gliomaspheres with $EC_{50}$ of 0.26 and 0.54 µM, respectively (FIG. 11A). SC-38 also potently attenuated growth of mesenchymal WK1 gliomaspheres ($EC_{50}$=0.91 µM, FIG. 11B). In the mesenchymal gliomaspheres, compound 1-18 was more efficacious ($EC_{50}$=2 µM) when compared to compound 1-08 ($EC_{50}$=3.82 µM).

The invention claimed is:

1. A compound selected from the group consisting of

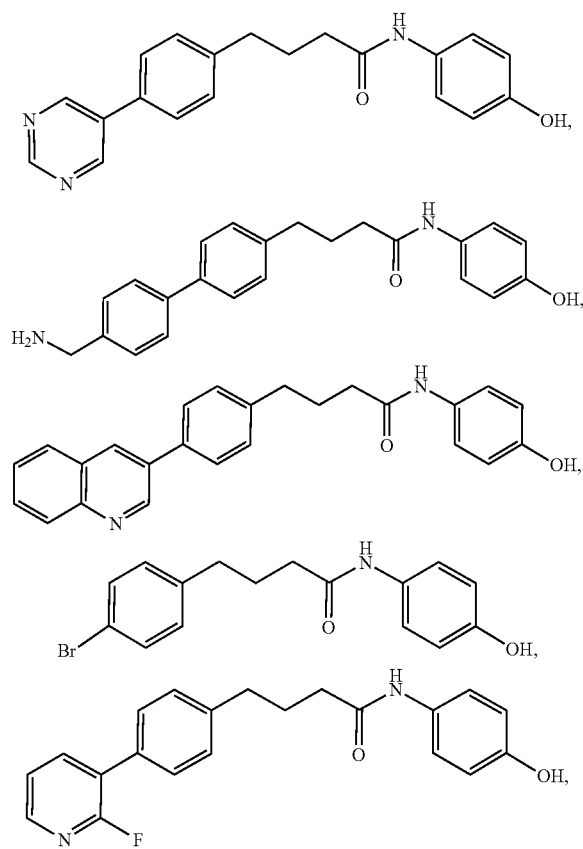

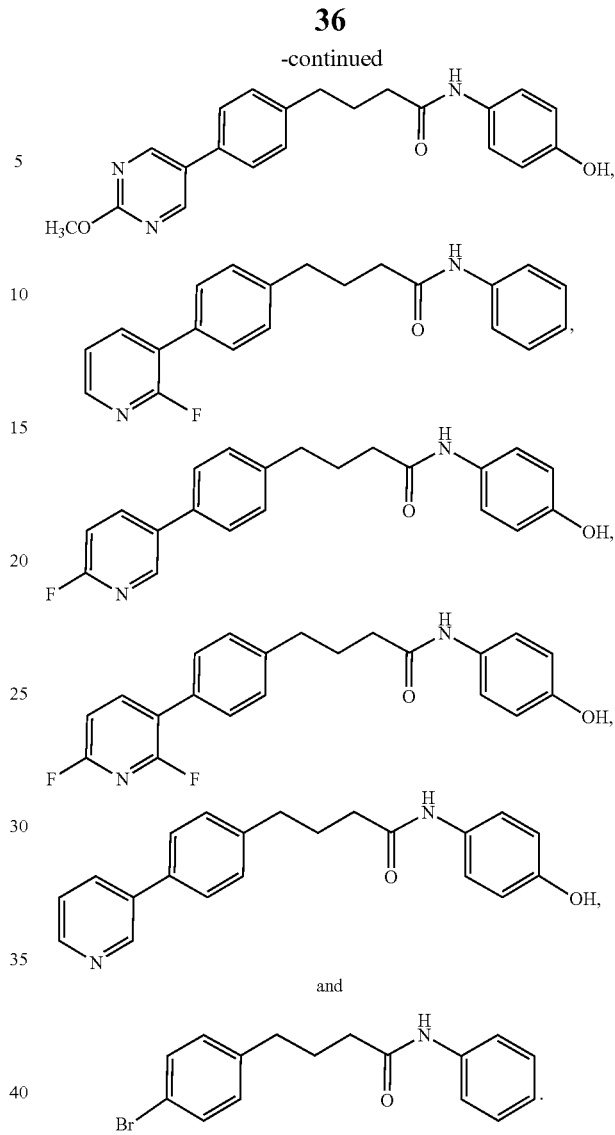

2. A pharmaceutical composition comprising the compound according to claim 1, together with a pharmaceutically acceptable carrier, diluent or excipient.

3. A method of treating a solid tumor in a subject in need thereof comprising administering to the subject a therapeutically effective amount of a compound according to claim 1.

4. A method of treating a solid tumor in a subject in need thereof comprising administering to the subject a pharmaceutical composition according to claim 2.

5. The method according to claim 3, wherein the solid tumor is a brain cancer.

6. The method according to claim 4, wherein the solid tumor is a brain cancer.

7. The method according to claim 5, wherein the brain cancer is selected from anaplastic astrocytoma, astrocytoma, central neurocytoma, choroid plexus carcinoma, choroid plexus papilloma, choroid plexus tumour, diffuse intrinsic pontine glioma, dysembryoplastic neuroepithelial tumour, ependymal tumour, fibrillary astrocytoma, giant-cell glioblastoma, glioblastoma multiforme, gliomatosis cerebri, gliosarcoma, hemangiopericytoma, medulloblastoma, medulloepithelioma, meningeal carcinomatosis, neuroblastoma, neurocytoma, oligoastrocytoma, oligodendroglioma, optic nerve sheath meningioma, paediatric ependymoma, pilocytic astrocytoma, pinealoblastoma, pineocytoma, pleomorphic anaplastic neuroblastoma, pleomorphic xanthoastrocytoma, primary central nervous system lymphoma, sphenoid wing meningioma, subependymal giant cell astrocytoma, subependymoma, and trilateral retinoblastoma.

8. The method according to claim 6, wherein the brain cancer is selected from anaplastic astrocytoma, astrocytoma, central neurocytoma, choroid plexus carcinoma, choroid plexus papilloma, choroid plexus tumour, diffuse intrinsic pontine glioma, dysembryoplastic neuroepithelial tumour, ependymal tumour, fibrillary astrocytoma, giant-cell glioblastoma, glioblastoma multiforme, gliomatosis cerebri, gliosarcoma, hemangiopericytoma, medulloblastoma, medulloepithelioma, meningeal carcinomatosis, neuroblastoma, neurocytoma, oligoastrocytoma, oligodendroglioma, optic nerve sheath meningioma, paediatric ependymoma, pilocytic astrocytoma, pinealoblastoma, pineocytoma, pleomorphic anaplastic neuroblastoma, pleomorphic xanthoastrocytoma, primary central nervous system lymphoma, sphenoid wing meningioma, subependymal giant cell astrocytoma, subependymoma, and trilateral retinoblastoma.

9. A method of preventing recurrence of a solid tumor in a subject, comprising administering to the subject an effective amount of a compound according to claim 1.

10. A method of preventing recurrence of a solid tumor in a subject, comprising administering to the subject a pharmaceutical composition according to claim 2.

11. The method according to claim 9, wherein the solid tumor is a brain cancer.

12. The method according to claim 10, wherein the solid tumor is a brain cancer.

13. The method according to claim 11, wherein the brain cancer is selected from anaplastic astrocytoma, astrocytoma, central neurocytoma, choroid plexus carcinoma, choroid plexus papilloma, choroid plexus tumour, diffuse intrinsic pontine glioma, dysembryoplastic neuroepithelial tumour, ependymal tumour, fibrillary astrocytoma, giant-cell glioblastoma, glioblastoma multiforme, gliomatosis cerebri, gliosarcoma, hemangiopericytoma, medulloblastoma, medulloepithelioma, meningeal carcinomatosis, neuroblastoma, neurocytoma, oligoastrocytoma, oligodendroglioma, optic nerve sheath meningioma, paediatric ependymoma, pilocytic astrocytoma, pinealoblastoma, pineocytoma, pleomorphic anaplastic neuroblastoma, pleomorphic xanthoastrocytoma, primary central nervous system lymphoma, sphenoid wing meningioma, subependymal giant cell astrocytoma, subependymoma and trilateral retinoblastoma.

14. The method according to claim 12, wherein the brain cancer is selected from anaplastic astrocytoma, astrocytoma, central neurocytoma, choroid plexus carcinoma, choroid plexus papilloma, choroid plexus tumour, diffuse intrinsic pontine glioma, dysembryoplastic neuroepithelial tumour, ependymal tumour, fibrillary astrocytoma, giant-cell glioblastoma, glioblastoma multiforme, gliomatosis cerebri, gliosarcoma, hemangiopericytoma, medulloblastoma, medulloepithelioma, meningeal carcinomatosis, neuroblastoma, neurocytoma, oligoastrocytoma, oligodendroglioma, optic nerve sheath meningioma, paediatric ependymoma, pilocytic astrocytoma, pinealoblastoma, pineocytoma, pleomorphic anaplastic neuroblastoma, pleomorphic xanthoastrocytoma, primary central nervous system lymphoma, sphenoid wing meningioma, subependymal giant cell astrocytoma, subependymoma and trilateral retinoblastoma.

* * * * *